United States Patent
Tal et al.

(10) Patent No.: US 12,186,089 B2
(45) Date of Patent: Jan. 7, 2025

(54) SYSTEMS AND METHODS FOR CONTROLLING A DEVICE BASED ON DETECTION OF TRANSIENT OSCILLATORY OR PSEUDO-OSCILLATORY BURSTS

(71) Applicant: Synchron Australia Pty Limited, Melbourne (AU)

(72) Inventors: Idan Tal, Los Angeles, CA (US); Peter Eli Yoo, Brooklyn, NY (US)

(73) Assignee: Synchron Australia Pty Limited, Dover, DE (US)

( * ) Notice: Subject to any disclaimer, the term of this patent is extended or adjusted under 35 U.S.C. 154(b) by 0 days.

(21) Appl. No.: 18/329,476

(22) Filed: Jun. 5, 2023

(65) Prior Publication Data

US 2023/0389851 A1 Dec. 7, 2023

Related U.S. Application Data

(60) Provisional application No. 63/480,746, filed on Jan. 20, 2023, provisional application No. 63/365,999, filed on Jun. 7, 2022.

(51) Int. Cl.
*A61B 5/374* (2021.01)
*A61B 5/00* (2006.01)
(Continued)

(52) U.S. Cl.
CPC .............. *A61B 5/374* (2021.01); *A61B 5/165* (2013.01); *A61B 5/293* (2021.01); *A61B 5/6868* (2013.01); *A61B 5/7267* (2013.01); *G06F 3/015* (2013.01)

(58) Field of Classification Search
CPC ......... A61B 5/374; A61B 5/165; A61B 5/293; A61B 5/6868; A61B 5/7267; G06F 3/015
See application file for complete search history.

(56) References Cited

U.S. PATENT DOCUMENTS 6,001,065 A * 12/1999 DeVito .................... G06F 3/015
                                                    341/20
8,805,494 B2    8/2014 Libbus et al.
(Continued)

FOREIGN PATENT DOCUMENTS

| JP | 2009-297474 | 12/2009 |
| WO | WO 2021/202915 | 10/2021 |
| WO | WO 2023/240043 | 12/2023 |

OTHER PUBLICATIONS

Caplan, J. et al. "Distinct Patterns of Brain Oscillations Underlie Two Basic Parameters of Human Maze Learning," *Journal of Neurophysiology*, 86(1), pp. 368-380, Jul. 1, 2001.
(Continued)

*Primary Examiner* — Rene T Towa
*Assistant Examiner* — Justin Xu
(74) *Attorney, Agent, or Firm* — Levine Bagade Han LLP

(57) ABSTRACT

Systems, methods, and apparatus for controlling a device based on the detection of transient oscillatory or pseudo-oscillatory bursts are disclosed. For example, a method can comprise detecting one or more transient oscillatory or pseudo-oscillatory bursts from an ongoing neural signal recording of a subject. The method can also comprise extracting one or more burst features from the one or more transient oscillatory or pseudo-oscillatory bursts detected within a detection period. The method can also comprise predicting a thought generated or conjured by the subject or a change in mental state evoked by the subject by applying at least one of a machine learning algorithm and a feature threshold to the one or more burst features extracted within the detection period. An input command associated with the prediction can be transmitted to the device in order to control the device.

29 Claims, 11 Drawing Sheets

(51) Int. Cl.
*A61B 5/16* (2006.01)
*A61B 5/293* (2021.01)
*G06F 3/01* (2006.01)
*G06N 3/0442* (2023.01)
*G06N 3/08* (2023.01)
*G06N 7/01* (2023.01)

(56) References Cited

U.S. PATENT DOCUMENTS

| | | | |
|---|---|---|---|
| 9,357,251 B2 | 5/2016 | Dove et al. | |
| 10,485,968 B2 | 11/2019 | Opie et al. | |
| 10,512,555 B2 | 12/2019 | John et al. | |
| 10,575,783 B2 | 3/2020 | Oxley | |
| 10,729,530 B2 | 8/2020 | Opie et al. | |
| 11,076,794 B2 | 8/2021 | Kozhaya et al. | |
| 11,550,391 B2 | 1/2023 | Yoo et al. | |
| 11,559,232 B1* | 1/2023 | Al-Saggaf | A61B 5/165 |
| 2004/0267320 A1* | 12/2004 | Taylor | G06F 3/016 607/2 |
| 2006/0189900 A1 | 8/2006 | Flaherty | |
| 2007/0032738 A1 | 2/2007 | Flaherty et al. | |
| 2009/0318826 A1* | 12/2009 | Green | A61B 5/7246 600/545 |
| 2010/0081958 A1* | 4/2010 | She | A61B 5/7232 327/344 |
| 2010/0130844 A1* | 5/2010 | Williams | A61B 5/291 607/116 |
| 2011/0307029 A1 | 12/2011 | Hargrove | |
| 2012/0172743 A1 | 7/2012 | Aguilar et al. | |
| 2012/0296476 A1 | 11/2012 | Cale et al. | |
| 2012/0310105 A1* | 12/2012 | Feingold | A61B 5/374 600/544 |
| 2014/0194719 A1* | 7/2014 | Frewin | A61B 5/24 600/377 |
| 2014/0288667 A1* | 9/2014 | Oxley | A61N 1/36067 607/45 |
| 2014/0309538 A1 | 10/2014 | More et al. | |
| 2015/0005660 A1 | 1/2015 | Kraus et al. | |
| 2015/0038869 A1 | 2/2015 | Simon et al. | |
| 2015/0272465 A1* | 10/2015 | Ishii | A61B 5/291 600/545 |
| 2015/0313490 A1 | 11/2015 | Archer et al. | |
| 2015/0313496 A1 | 11/2015 | Connor | |
| 2015/0317817 A1 | 11/2015 | Ryu | |
| 2015/0338917 A1 | 11/2015 | Steiner et al. | |
| 2015/0351655 A1 | 12/2015 | Coleman | |
| 2016/0235324 A1 | 8/2016 | Mershin et al. | |
| 2016/0242690 A1 | 8/2016 | Principe et al. | |
| 2017/0171441 A1 | 6/2017 | Kearns et al. | |
| 2018/0071648 A1 | 3/2018 | Chhatlani et al. | |
| 2018/0160982 A1 | 6/2018 | Laszlo et al. | |
| 2018/0178009 A1 | 6/2018 | Lee et al. | |
| 2018/0292902 A1 | 10/2018 | Min | |
| 2018/0303595 A1 | 10/2018 | Opie et al. | |
| 2019/0038438 A1* | 2/2019 | John | G06F 3/015 |
| 2019/0058703 A1 | 2/2019 | Zhu | |
| 2019/0104968 A1 | 4/2019 | Fedele | |
| 2019/0113973 A1 | 4/2019 | Coleman et al. | |
| 2019/0166434 A1 | 5/2019 | Petley et al. | |
| 2019/0336748 A1 | 11/2019 | Oxley | |
| 2020/0016396 A1 | 1/2020 | Yoo | |
| 2020/0061378 A1 | 2/2020 | Ganguly et al. | |
| 2020/0078195 A1 | 3/2020 | John et al. | |
| 2020/0205741 A1* | 7/2020 | Laszlo | A61B 5/165 |
| 2020/0329990 A1 | 10/2020 | Laszlo et al. | |
| 2020/0363869 A1 | 11/2020 | Yoo | |
| 2020/0364539 A1* | 11/2020 | Anisimov | G06F 3/011 |
| 2021/0055794 A1* | 2/2021 | Lee | G06F 3/015 |
| 2021/0064135 A1 | 3/2021 | Shenoy et al. | |
| 2021/0124419 A1* | 4/2021 | Kang | G06N 3/045 |
| 2021/0361222 A1 | 11/2021 | Elbogen et al. | |
| 2021/0361950 A1 | 11/2021 | Opie et al. | |
| 2021/0365117 A1 | 11/2021 | Yoo et al. | |
| 2022/0137702 A1* | 5/2022 | Min | G06F 3/011 345/156 |
| 2022/0175555 A1* | 6/2022 | Robison | G06F 3/015 |
| 2023/0001585 A1* | 1/2023 | Nam | B25J 11/0005 |
| 2023/0107850 A1 | 4/2023 | Yoo et al. | |

OTHER PUBLICATIONS

Felsenstein, O. et al. "Decoding multimodal behavior using time differences of MEG events," accessed at: https://www.researchgate.net/publication/330617446_Decoding_multimodal_behavior_using_time_differences_of_MEG_events, 25 pages, Jan. 2019.

Jones, S. "When brain rhythms aren't 'rhythmic': implication for their mechanisms and meaning," *Current Opinion in Neurobiology*, vol. 40, pp. 72-80, Oct. 2016.

Karvat, G. et al. "Real-time detection of neural oscillation bursts allows behaviourally relevant neurofeedback," *Communications Biology*, 3(72), 10 pages, Feb. 14, 2020.

Lakatos, P. et al. "Attention and arousal related modulation of spontaneous gamma-activity in the auditory cortex of the cat," *Cognitive Brain Research*, 19(1), pp. 1-9, Mar. 2004.

Lundqvist, M. et al. "Gamma and beta bursts underlie working memory," *Neuron*, 90(1), pp. 152-164, Apr. 6, 2016.

Neymotin, S. et al. "Detecting Spontaneous Neural Oscillation Events in Primate Auditory Cortex," *eNeuro*, 9(4), 20 pages, Jul. 29, 2022.

Quinn, A. et al. "Unpacking Transient Event Dynamics in Electrophysiological Power Spectra," *Brain Topography*, vol. 32, pp. 1020-1034, Nov. 21, 2019.

Sherman, M. et al. "Neural mechanisms of transient neocortical beta rhythms: Converging evidence from humans, computational modeling, monkeys, and mice," *PNAS*, 113(33), 10 pages, Jul. 28, 2016.

Shin, H. et al. "The rate of transient beta frequency events predicts behavior across tasks and species," *Neuroscience*, 31 pages, Nov. 6, 2017.

Tal, I. et al. "Imaging the Spatiotemporal Dynamics of Cognitive Processes at High Temporal Resolution," *Neural Computation*, 30(3), pp. 610-630, Mar. 2018.

Tal, I. et al. "Temporal accuracy of human cortico-cortical interactions," *Journal of Neurophysiology*, vol. 115, pp. 1810-1820, Feb. 3, 2016.

\* cited by examiner

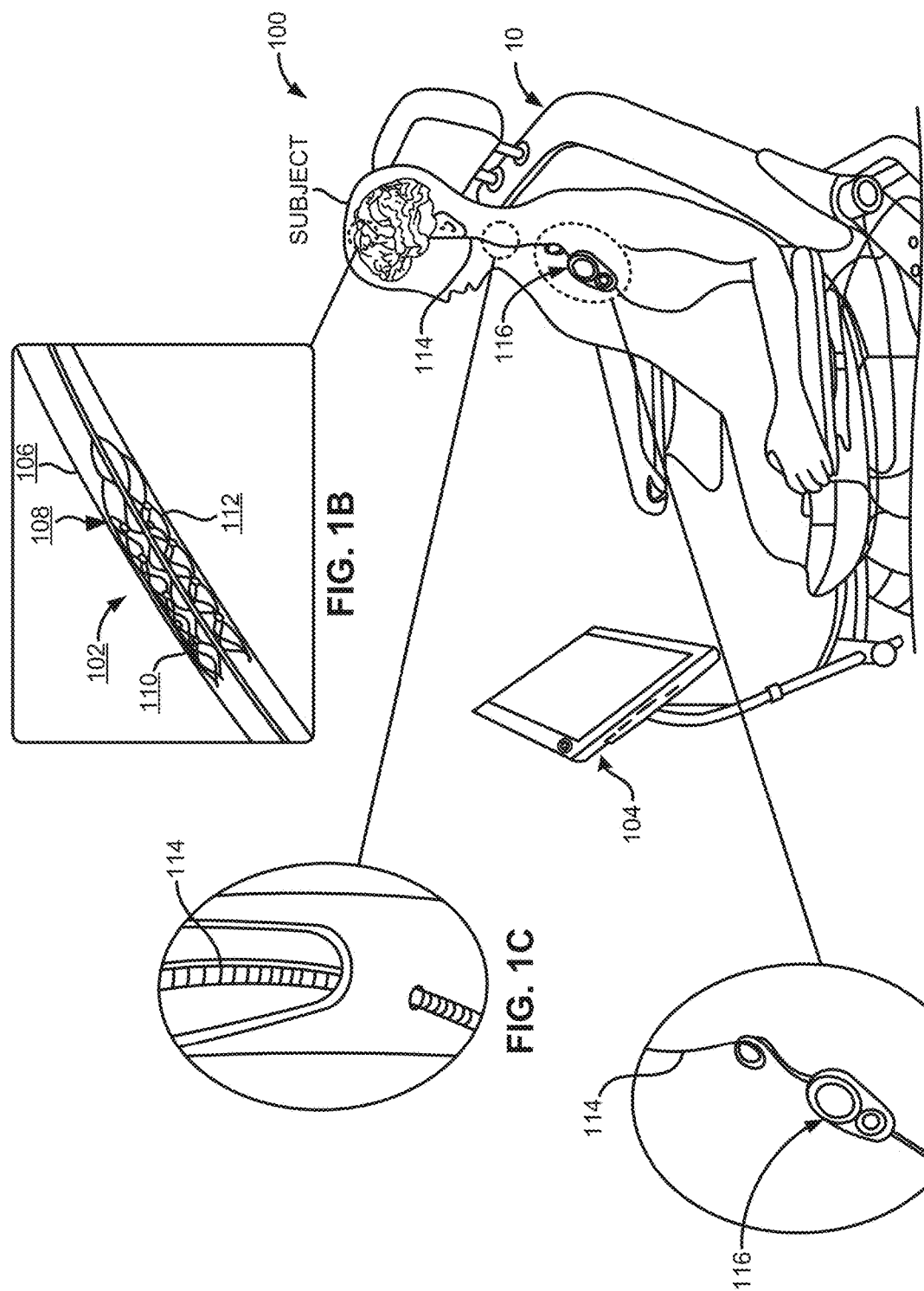

|  | precision | recall | f1-score | support |
|---|---|---|---|---|
| Both_ankle_mov | 0.93 | 0.68 | 0.79 | 1492 |
| Rest | 0.74 | 0.95 | 0.83 | 1456 |
| accuracy |  |  | 0.81 | 2948 |
| macro avg | 0.84 | 0.82 | 0.81 | 2948 |
| weighted avg | 0.84 | 0.81 | 0.81 | 2948 | total duration: 294.8 s
total clicks: 1014
click rate: 3.4396200814111126 s~-1

SYSTEMS AND METHODS FOR CONTROLLING A DEVICE BASED ON DETECTION OF TRANSIENT OSCILLATORY OR PSEUDO-OSCILLATORY BURSTS

CROSS-REFERENCE TO RELATED APPLICATIONS

This application claims the benefit of U.S. Provisional Patent Application No. 63/480,746 filed on Jan. 20, 2023 and U.S. Provisional Patent Application No. 63/365,999 filed on Jun. 7, 2022, the contents of which are incorporated herein by reference in their entireties.

TECHNICAL FIELD

This disclosure relates generally to brain-computer interfaces and, more specifically, to systems and methods for controlling a device based on the detection of transient oscillatory or pseudo-oscillatory bursts.

BACKGROUND

It has been shown that people with mobility limitations can use brain-computer interfaces (BCIs) to control personal electronic or computing devices, internet of things (IoT) devices, software, and mobility vehicles. An effective BCI should allow people with the entire spectrum of mobility limitations to effectively control such devices, including those with severe mobility limitations such as locked-in patients that may only have control over certain neural functions such as generating or conjuring thoughts. The goal of an effective BCI is to extract features from neural signal recordings that correlate to distinct mental and/or physical thoughts, states, or conditions of a subject and to be able to identify those thoughts, states, or conditions for utilization. However, there are several problems associated with this goal.

First, neural activity sampled by sensors often yield noisy signals where the change in such signals correlating to a subject's mental or physical state is better observed when the signal is averaged across many trials of the subject generating or achieving the same mental or physical state. This practice is sometimes referred to as "averaging across." Averaging over repetitions of a task is also commonly used to create a template of the signal based on the average, that can later be matched with the ongoing signal to achieve real-time identification and classification of the signal. The downside to analyzing neural signals by averaging across is that the subject is often asked to achieve the same mental or physical state repeatedly in order for the BCI system to overcome the low signal-to-noise ratio. However, in order for any BCI system to be truly useful to a subject, the system must be able to detect characteristic changes in the subject's neural signals in real-time or in an ongoing recording.

Second, the overall power of an oscillatory signal is often calculated over a detection period spanning several seconds to highlight the changes in the signal as the subject comes in and out of a mental and/or physical state. However, because the power is calculated across this detection period, the BCI system will often lose more fine-grained transient changes in the signal that may be characteristic of certain mental and/or physical thoughts, states, or conditions of the subject.

Third, most traditional BCI systems are only able to take advantage of a few features extracted from a subject's neural signal recordings. A more robust BCI system should be able to access multiple features that can then be used to correlate such detected features with the subject's various mental and/or physical states. Moreover, some traditional BCI systems are only able to make a classification decision based on longer periods of time by considering properties of the signal over longer windows of data, resulting in fewer examples for training a learning algorithm. A more robust BCI system should be able to make classification decisions based on shorter segments of data to achieve both faster classification and more training examples for a learning algorithm. Some BCI systems may overcome some of these limitations by applying more sophisticated algorithms to the raw neural signal and have the algorithm determine the most informative aspects of the signal. However, such systems may require a lot of data from each participant for training for the algorithm to pick up on those informative aspects of the neural signal. On many occasions, such large amounts of data may not be available. In addition, the approach of using the raw data as an input to the classification algorithm may carry the risk of using noise sources for classification instead of actual brain signals, since the algorithms are often blind to the distinction between brain signals and noise sources. Thus, a more robust BCI system would take advantage of neuroscientific knowledge to extract the informative features from the neural signals before applying the classification algorithm.

The inability to pick up more fine-grained transient changes in a subject's neural signals is problematic given that researchers have begun to look into the importance of transient changes or burst-like events that can be detected from a subject's ongoing or real-time neural recording. For example, some researchers have found that spontaneous neocortical beta rhythms emerged as non-continuous beta events that do not necessarily depend on rhythmic inputs but on the relative timing and strength of synchronous proximal and distal drives (see Sherman et al. "Neural mechanisms of transient neocortical beta rhythms: converging evidence from humans, computational modeling, monkeys, and mice." *Proc Natl Acad Sci USA* 113 (2016): E4885-E4894). Others have shown that differences in the rate of beta events could be used to predict the detection of stimuli at a perceptual threshold and that non-detectable trials were more likely to have a beta event within −200 milliseconds prior to the stimulus (see Shin et al. "The rate of transient beta frequency events predicts behavior across tasks and species." *Elife* 6 (2017): e29086). Researchers have also used a trial-by-trial analysis and found that brief bursts of gamma-band activity accompanied encoding and re-activation of sensory information in recording sites associated with spiking that reflected "to be remembered" items (Lundqvist et al. "Gamma and beta bursts underlie working memory." *Neuron* 90.1 (2016): 152-164). Moreover, some researchers have noted that transient events might form more complex repeating sequences of activation with millisecond precision suggesting that relevant information might be encoded by subtle time differences or cascades of transient events across the brain (see Felsenstein et al. "Decoding multimodal behavior using time differences of MEG events." arXiv preprint: 1901.08093 (2019); Tal, Idan, and Moshe Abeles. "Temporal accuracy of human cortico-cortical interactions." *Journal of Neurophysiology* 115.4 (2016): 1810-1820; and Tal, I., and M. Abeles. "Imaging the spatiotemporal dynamics of cognitive processes at high temporal resolution." *Neural Computation* 30.3 (2018): 610-630).

Therefore, improvements in the field of BCI are needed that leverage these new discoveries concerning the importance of transient burst-like events that can be detected from a subject's ongoing neural signal. Moreover, any such improved BCI systems should also address the previously discussed shortcomings with traditional BCI systems. Such a system should allow a patient with severe mobility limitations to maintain or retain their independence even when such patients only have control over their thoughts or mental state.

SUMMARY

Systems and methods for controlling a device based on the detection of transient oscillatory or pseudo-oscillatory bursts are disclosed.

In some aspects, a method of controlling a device is disclosed. The method comprising: detecting one or more transient oscillatory or pseudo-oscillatory bursts from an ongoing or real-time neural signal recording of a subject captured by a recording device, wherein at least some of the one or more transient oscillatory or pseudo-oscillatory bursts are generated in response to a thought generated or conjured by the subject or a change in mental state evoked by the subject; extracting, using one or more processors of a computing device communicatively coupled to the recording device, one or more burst features from the one or more transient oscillatory or pseudo-oscillatory bursts detected within a detection period; and predicting, using the one or more processors, the thought generated or conjured by the subject or the change in mental state evoked by the subject by applying at least one of a machine learning algorithm and a feature threshold to the one or more burst features extracted within the detection period; and transmitting an input command associated with the prediction to the device in order to control the device.

In some aspects, the ongoing or real-time neural signal recording of the subject can be made by recording raw electrical signals from the brain of the subject using the recording device, and wherein detecting the one or more transient oscillatory or pseudo-oscillatory bursts further comprises: filtering the raw electrical signals in one or more desired frequency bands using one or more frequency decomposition methods such as at least one of a bandpass filter and a wavelet convolution; converting voltage values of the filtered raw electrical signals into magnitude or power-related values for each of the desired frequency bands; applying at least one of a power threshold to the magnitude or power-related values for each of the desired frequency bands and a duration threshold for each of the desired frequency bands; and identifying one of the transient oscillatory or pseudo-oscillatory bursts in response to at least one of the magnitude or power-related values exceeding the power threshold and a duration of one of the raw electrical signals exceeding the duration threshold for each of the desired frequency bands.

In some aspects, the at least one of the power threshold and the duration threshold can be selected based on at least one training session conducted with the subject, wherein the at least one training session comprises: instructing or prompting the subject to generate or conjure the thought or evoke the change in the mental state of the subject; recording the raw electrical signals from the brain of the subject using the recording device after prompting the subject to generate or conjure the thought; filtering the raw electrical signals in the one or more desired frequency bands using one or more frequency decomposition methods such as at least one of the bandpass filter and the wavelet convolution; converting the voltage values of the filtered raw electrical signals into power values for each of the desired frequency bands; and selecting the at least one of the power threshold and the duration threshold for each of the desired frequency bands in order to distinguish the transient oscillatory or pseudo-oscillatory bursts from background noise.

In some aspects, a system for controlling a device is disclosed. The system comprising a recording device configured to capture an ongoing or real-time neural signal recording of a subject and a computing device having one or more processors communicatively coupled to the recording device. In these aspects, the one or more processors of the computing device can be programmed to: detect one or more transient oscillatory or pseudo-oscillatory bursts from the ongoing or real-time neural signal recording of the subject, wherein the one or more transient oscillatory or pseudo-oscillatory bursts are generated in response to a thought generated or conjured by the subject or a change in mental state evoked by the subject, extract one or more burst features from the one or more transient oscillatory or pseudo-oscillatory bursts detected within a detection period, and predict the thought generated or conjured by the subject or the change in mental state evoked by the subject by applying at least one of a machine learning algorithm and a feature threshold to the one or more burst features extracted within the detection period, and transmit an input command associated with the prediction to the device in order to control the device.

In some aspects, the recording device can be configured to capture the ongoing or real-time neural signal recording of the subject by recording raw electrical signals from the brain of the subject. In these aspects, the one or more processors of the computing device can be programmed to: filter the raw electrical signals in one or more desired frequency bands using one or more frequency decomposition methods; convert voltage values of the filtered raw electrical signals into magnitude or power-related values for each of the desired frequency bands; apply at least one of a power threshold to the magnitude or power-related values for each of the desired frequency bands and a duration threshold for each of the desired frequency bands; and identify one of the transient oscillatory or pseudo-oscillatory bursts in response to at least one of the magnitude or power-related values exceeding the power threshold and the filtered raw electrical signals exceeding the duration threshold for each of the desired frequency bands.

In some aspects, the at least one of the power threshold and the duration threshold can be selected based on at least one training session conducted with the subject using the computing device or another device and the recording device. The computing device or the other device can be configured to instruct or prompt the subject to generate or conjure the thought or evoke the change in the mental state of the subject. The recording device can be configured to record the raw electrical signals from the brain of the subject after the subject is prompted to generate or conjure the thought. The one or more processors of the computing device can be programmed to: filter the raw electrical signals in the one or more desired frequency bands using one or more frequency decomposition methods; convert the voltage values of the filtered raw electrical signals into power values for each of the desired frequency bands; and select the at least one of the power threshold and the duration threshold to be applied for each of the desired frequency bands in order to distinguish the transient oscillatory or pseudo-oscillatory bursts from background noise.

In some aspects, the desired frequency bands comprise frequency bands between 0.1 Hz and 32 kHz (also, e.g., between 4 Hz and 400 Hz).

In some aspects, the desired frequency bands comprise at least one of a beta frequency band, a gamma frequency band, and a high-gamma frequency band.

In some aspects, the one or more burst features comprise a burst rate, wherein the burst rate can be calculated by dividing a burst count by a length of the detection period.

In some aspects, the burst count can be calculated by summing all of the transient oscillatory or pseudo-oscillatory bursts detected across all electrodes, or a subset of electrodes, of the recording device within the detection period.

In some aspects, the feature threshold can be a burst rate threshold.

In some aspects, the burst rate threshold can be a median burst rate calculated from previous detection periods.

In some aspects, the one or more burst features comprise at least one of a burst count, a burst rate, a burst band frequency or frequency distribution, an interburst interval length, a burst timing or timing pattern, an average burst duration, a burst waveform, and any changes thereof.

In some aspects, the machine learning algorithm can be a neural network.

In some aspects, the neural network can be a recursive neural network.

In some aspects, the recursive neural network can be a long short-term memory (LSTM) neural network.

In some aspects, the feature threshold can be a static threshold.

In some aspects, the feature threshold can be a dynamic threshold adjusted over time by the computing device. The certain aspects, the feature threshold can require crossing a threshold for a specific duration.

In some aspects, the detection period can be between 1 ms and 100 ms. In other aspects, the detection period can be between 10 ms and 100 ms.

In some aspects, the device can be at least one of a personal computing device, an internet-of-things (IoT) device, and a mobility vehicle.

In some aspects, the device can be the personal computing device, and the input command can be a command to initiate a click of a cursor of the personal computing device.

In some aspects, the thought of the subject can be a thought generated or conjured by the subject to move one or more body parts of the subject.

In some aspects, the thought can be generated or conjured by the subject without the subject being prompted to do so such that control of the device is conducted asynchronously.

In some aspects, the thought can be generated or conjured by the subject in response to the subject being prompted to do so such that control of the device is conducted synchronously.

In some aspects, the recording device can be a non-invasive recording device. For example, the recording device can be an electroencephalography (EEG) device.

In some aspects, the recording device can be an invasive recording device.

In some aspects, the recording device can be an endovascular recording device configured to be implanted within a vein or sinus of the brain of the subject.

In some aspects, the endovascular recording device can be an electrode array including a plurality of electrodes carried by an expandable stent or scaffold.

In some aspects, the one or more transient oscillatory or pseudo-oscillatory bursts can be detected using the electrodes carried by the expandable stent or scaffold, and wherein the method further comprises applying a weighting factor to one or more electrodes of the expandable stent or scaffold such that the transient oscillatory or pseudo-oscillatory bursts detected at the one or more electrodes are weighted more than the transient oscillatory or pseudo-oscillatory bursts detected at another electrode of the expandable stent or scaffold.

In some aspects, the recording device can be an implantable microelectrode array (MEA). For example, the recording device can be a Utah microelectrode array or a Michigan microelectrode array.

In some aspects, the recording device can be an electrode array that can be implanted on a brain surface or a surface of the cortex. For example, the recording device can be an electrocorticography (eCoG) electrode array.

In some aspects, the recording device can be a thin-film electrode array or thin-film microelectrodes.

In some aspects, the machine learning algorithm can be trained using previous predictions made by the machine learning algorithm and the burst features extracted from previous detection periods to enhance predictions made by the machine learning algorithm.

BRIEF DESCRIPTION OF THE DRAWINGS

FIG. 1A illustrates one embodiment of a brain-computer interface (BCI) system configured to control a device based on the detection of transient oscillatory or pseudo-oscillatory bursts from an ongoing or real-time neural signal recording of a subject.

FIG. 1B illustrates one embodiment of a recording device of the BCI system implemented as a stent-electrode array comprising a plurality of electrodes.

FIG. 1C illustrates that a communication conduit can connect the stent-electrode array with a telemetry unit communicatively coupled to a computing device of the BCI system.

FIG. 1D illustrates a close-up view of an embodiment of the telemetry unit.

DETAILED DESCRIPTION

Figure 2A:
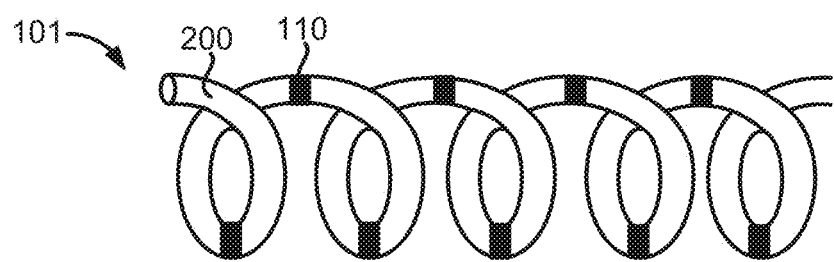
FIG. 2A illustrates another embodiment of an implantable recording device implemented as a coiled wire comprising a plurality of electrodes.

FIG. 1A illustrates one embodiment of a brain-computer interface (BCI) system 100 configured to control a device 10 based on the detection of transient oscillatory or pseudo-oscillatory bursts 302 from an ongoing or real-time neural signal recording (see FIG. 3A) of a subject. The BCI system 100 disclosed herein can be used by the subject (e.g., an individual with a mobility issue) to control a device 10 such as a personal computing device, an internet-of-things (IoT) device, a mobility vehicle (e.g., a wheelchair), or a combination thereof.

The BCI system 100 can transmit an input command 312 (see FIG. 3A) to the device 10 to control the device 10. For example, when the device 10 is a personal computing device, the input command 312 can be a command to initiate a click of a cursor of the personal computing device. In other embodiments, the input command 312 can be a command to maneuver or operate the mobility vehicle (e.g., the wheelchair) carrying the subject.

The system 100 can comprise a recording device 102 (see FIG. 1B) and a computing device 104. The recording device 102 can be configured to record a brain activity of the subject. In some embodiments, the recording device 102 can be an invasive recording device 102 configured to be implanted within a brain vessel 106 of the subject.

For example, the recording device 102 can be a stent-electrode array 108 configured to be implanted within a brain vessel 106 of the subject (see, e.g., FIG. 1B). As a more specific example, the recording device 102 can be implanted within a cortical or cerebral vein or sinus of the subject.

In some embodiments, the recording device 102 can be an implantable microelectrode array (MEA). For example, the recording device 102 can be a Utah microelectrode array or a Michigan microelectrode array.

In some embodiments, the recording device 102 can be a thin-film electrode array or comprised of thin-film microelectrodes.

In some embodiments, the recording device 102 can be an electrode array that can be implanted on a brain surface or a surface of the cortex. For example, the recording device 102 can be an electrocorticography (eCoG) electrode array (see, e.g., FIG. 2D).

In some embodiments, the recording device 102 can be a non-invasive recording device such as an electroencephalography (EEG) device, helmet, or other type of headgear.

FIG. 1B illustrates that the stent-electrode array 108 can comprise a plurality of electrodes 110 affixed, secured, or otherwise coupled to an exterior portion or radially outer portion of an expandable stent 112 or scaffold serving as an endovascular carrier for the electrode array. For example, the electrodes 110 can be arranged along filaments making up the walls, rings, or scaffold of the expandable stent 112.

In some embodiments, the recording device 102 can comprise typically between 8 to 24 electrodes. For example, the recording device 102 can comprise 16 electrodes. In other embodiments, the recording device 102 can comprise between 24 and 64 electrodes 110.

In some embodiments, the filaments of the expandable stent 112 can be made in part of a shape-memory alloy. For example, the filaments of the expandable stent 112 can be made in part of Nitinol or Nitinol wire. The filaments of the expandable stent 112 can also be made in part of stainless steel, gold, platinum, nickel, titanium, tungsten, aluminum, nickel-chromium alloy, gold-palladium-rhodium alloy, chromium-nickel-molybdenum alloy, iridium, rhodium, or a combination thereof.

In alternative embodiments, the filaments of the expandable stent 112 can also be made in part of a shape memory polymer.

The electrodes 110 can be made in part of platinum, platinum black, gold, iridium, palladium, rhodium, or alloys or composites thereof (e.g., a gold-palladium-rhodium alloy or composite). In certain embodiments, the electrodes 110 can be made of a metal alloy or composite with a high charge injection capacity (e.g., a platinum-iridium alloy or composite).

The electrodes 110 can be shaped as circular disks having a disk diameter of between about 100 μm to 1.0 mm. In other embodiments, the electrodes 110 can have a disk diameter of between 1.0 mm and 1.5 mm. In other embodiments, the electrodes 110 can be cylindrical, spherical, cuff-shaped, ring-shaped, partially ring-shaped (e.g., C-shaped), or semi-cylindrical.

In other embodiments, the stent-electrode array 108 can be any of the stents, scaffolds, stent-electrodes, or stent-electrode arrays disclosed in U.S. Patent Pub. No. 2021/0365117; U.S. Patent Pub. No. 2021/0361950; U.S. Patent Pub. No. 2020/0363869; U.S. Patent Pub. No. 2020/0078195; U.S. Patent Pub. No. 2020/0016396; U.S. Patent Pub. No. 2019/0336748; U.S. Patent Pub. No. US 2014/0288667; U.S. Pat. Nos. 10,575,783; 10,485,968; 10,729,530; and 10,512,555; the contents of which are incorporated herein by reference in their entireties.

When the recording device 102 (e.g., the stent-electrode array 108) is implanted within a brain vessel 106 of the subject, each of the electrodes 110 of the recording device 102 can be configured to read or record the electrical activities of neurons within a vicinity of each electrode 110. The electrical activities of neurons can be recorded as raw electrical signals. As will be discussed in more detail in later sections, the raw electrical signals can be filtered and processed to detect one or more transient oscillatory or pseudo-oscillatory bursts 302.

The raw electrical signals can be divided into bands by their frequency. For example, the desired frequency bands comprise frequency bands between 0.1 Hz and 32 kHz. The transient oscillatory or pseudo-oscillatory bursts 302 detected from these signals can also be associated with such frequency bands. For example, the transient oscillatory or pseudo-oscillatory bursts 302 can be referred to as beta bursts or beta-band bursts if these bursts were obtained from signals in the beta-oscillatory band (having a frequency of approximately 15-35 Hz). In addition, the transient oscillatory or pseudo-oscillatory bursts 302 can be referred to as gamma bursts or gamma-band bursts if these bursts were obtained from signals in the gamma-oscillatory band (having a frequency of approximately 45-100 Hz). Moreover, the transient oscillatory or pseudo-oscillatory bursts 302 can be referred to as alpha bursts or alpha-band bursts if these bursts were obtained from signals in the alpha-oscillatory band (having a frequency of approximately 7 Hz to 12 Hz). Furthermore, the transient oscillatory or pseudo-oscillatory bursts 302 can be referred to as theta bursts or theta-band bursts if these bursts were obtained from signals in the theta-oscillatory band (having a frequency of approximately 4 Hz to 7 Hz).

In some embodiments, the recording device 102 can be implanted within a cerebral or cortical vein or sinus of the subject. For example, the recording device 102 can be implanted within a superior sagittal sinus, an inferior sagittal sinus, a sigmoid sinus, a transverse sinus, a straight sinus, a superficial cerebral vein such as a vein of Labbe, a vein of Trolard, a Sylvian vein, a Rolandic vein, a deep cerebral vein such as a vein of Rosenthal, a vein of Galen, a superior thalamostriate vein, an inferior thalamostriate vein, or an internal cerebral vein, a central sulcal vein, a post-central sulcal vein, or a pre-central sulcal vein. In certain embodiments, the recording device 102 can be implanted within a vessel extending through the hippocampus or amygdala of the subject.

Alternatively or additionally, the recording device 102 can be an implantable microelectrode array (MEA). For example, the recording device 102 can be a Utah microelectrode array or a Michigan microelectrode array.

The recording device 102 can also be a thin-film electrode array or comprised of thin-film microelectrodes.

FIG. 1C illustrates that a communication conduit 114 (e.g., a lead wire) can connect the implantable recording device 102 (e.g., the stent-electrode array 108) with a telemetry unit 116 communicatively coupled to the computing device 104. Alternatively, a communication conduit 114 can connect the implantable recording device 102 directly with the computing device 104.

The communication conduit 114 can be a biocompatible lead wire or cable. When the recording device 102 is a stent-electrode array 108 deployed within a brain vessel 106 (e.g., the superior sagittal sinus) of the subject, the communication conduit 114 can extend through one or more brain vessels and out through a wall of a vein coupled to at least one of the brain vessels (e.g., the internal jugular vein) of the subject. The communication conduit 114 can then tunnel under the skin of the subject to a region of the subject (e.g., beneath the pectoralis major muscle) where the telemetry unit 116 is implanted.

FIG. 1D illustrates a close-up view of an embodiment of the telemetry unit 116. In some embodiments, the telemetry unit 116 can be configured to transmit signals received from the recording device 102 to the computing device 104 for processing and analysis. The telemetry unit 116 can also serve as a communication hub between the recording device 102 and the computing device 104.

In certain embodiments, the telemetry unit 116 can be an internal telemetry unit 116 implantable under the skin of the subject. For example, the telemetry unit 116 can be implanted within a pectoral region or within a subclavian space of the subject.

In other embodiments, the telemetry unit 116 can be an external telemetry unit 116 not implanted within the subject. In these embodiments, the communication conduit 114 can extend through the skin of the subject to connect to the telemetry unit 116. In additional embodiments, the telemetry unit 116 can comprise both an implantable portion and an external portion.

In some embodiments, the telemetry unit 116 can transmit data or signals to the computing device 104 or receive data or commands from the computing device 104 via a wired connection. In other embodiments, the telemetry unit 116 can transmit data or signals to the computing device 104 or receive data or commands from the computing device 104 via a wireless communication protocol such as Bluetooth™, Bluetooth Low Energy (BLE), ZigBee™, WiFi, or a combination thereof.

As will be discussed in more detail in later sections, one or more processors of the computing device 104 can be programmed to detect one or more transient oscillatory or pseudo-oscillatory bursts 302 from an ongoing or real-time neural signal recording of the subject captured by the recording device 102. At least some of the one or more transient oscillatory or pseudo-oscillatory bursts 302 can be generated in response to a thought generated or conjured by the subject or a change in a mental state evoked by the subject. Moreover, the one or more processors of the computing device 104 can also be programmed to extract one or more burst features 400 (see FIG. 4) from the one or more transient oscillatory or pseudo-oscillatory bursts 302 detected within a detection period 404 or detection window. Furthermore, the one or more processors of the computing device 104 can be programmed to predict the thought generated or conjured by the subject or the change in mental state of the subject by applying a feature threshold 310 and/or a machine learning algorithm 308 (see FIG. 3A) (e.g., a deep learning algorithm) to the one or more burst features 400 extracted within the detection period 404. The one or more processors of the computing device 104 can then transmit an input command 312 associated with the prediction to the device 10 in order to control the device 10.

In some embodiments, one or more processors of the telemetry unit 116 can be programmed to detect one or more transient oscillatory or pseudo-oscillatory 302 from an ongoing or real-time neural signal recording of the subject captured by the recording device 102. At least one or more of the transient oscillatory or pseudo-oscillatory 302 can be generated in response to a thought generated or conjured by the subject or a change in a mental state evoked by the subject. Moreover, the one or more processors of the telemetry unit 116 can also be programmed to extract one or more burst features 400 from the one or more transient oscillatory or pseudo-oscillatory bursts 302 detected within a detection period 404. Furthermore, the one or more processors of the telemetry unit 116 can be programmed to predict the thought generated or conjured by the subject or the change in mental state evoked by the subject by applying a feature threshold 310 and/or a machine learning algorithm 308 to the one or more burst features 400 extracted within the detection period 404. The one or more processors of the telemetry unit 116 can then transmit an input command 312 associated with the prediction to the computing device 104 or directly to the device 10 in order to control the device 10.

The transient oscillatory or pseudo-oscillatory bursts 302 can be generated in response to a thought generated, conjured, or invoked by the subject or a change in mental state evoked by the subject.

In some embodiments, the thought can be a thought generated or conjured by the subject to command the device 10 (including a component thereof or a software application running thereon). As a more specific example, the thought generated or conjured by the subject can be a thought to move a cursor shown on a display of a personal computing device serving as the device 10. As another example, the thought generated or conjured by the subject can be a thought to move a mobility vehicle (e.g., a wheelchair carrying the subject) serving as the device 10. In these instances, the thought can be referred to as a task-relevant thought.

As an additional example, the change in mental state evoked by the subject can involve the subject focusing their attention on the cursor or focusing their attention on the mobility vehicle. In these instances, the change in mental state can be referred to as a task-relevant mental state change.

In other embodiments, the thought can be a thought generated or conjured by the subject that is unrelated to or is disconnected from commanding the device 10 (including any components thereof or software applications running thereon). As a more specific example, the thought generated or conjured by the subject can be a thought to move one or more body parts (e.g., hand(s), fingers, ankle(s), foot/feet, toe(s), leg(s), arm(s), head, etc.) of the subject. Also, for example, the thought generated or conjured by the subject can be a thought to tense or untense one or more body parts of the subject (e.g., tense or untense one or more muscles or muscle groups of the subject). In these instances, the thought can be referred to as a task-irrelevant thought.

Moreover, the change in mental state evoked by the subject can involve the subject focusing their attention on one or more body parts of the subject or focusing their attention on a task other than commanding the device 10 (including any components thereof or software applications running thereon). In these instances, the change in mental state can be referred to as a task-irrelevant mental state change.

As an additional example, the change in mental state evoked by the subject can involve the subject focusing their attention on the cursor or focusing their attention on the mobility vehicle. In these instances, the change in mental state can be referred to as a task-relevant mental state change.

FIG. 2A illustrates another embodiment of the implantable recording device 102 as a coiled wire 200 comprising a plurality of electrodes 110. The coiled wire 200 can serve as the endovascular carrier for the electrodes 110 and can be used in vessels that are too small to accommodate the stent-electrode array 108.

The coiled wire 200 can be a biocompatible wire or microwire configured to wind itself into a coiled pattern or a substantially helical pattern. The electrodes 110 can be arranged such that the electrodes 110 are scattered along a length of the coiled wire 200. More specifically, the electrodes 110 can be affixed, secured, or otherwise coupled to distinct points along a length of the coiled wire 200.

The electrodes 110 can be separated from one another such that no two electrodes 110 are within a predetermined separation distance (e.g., at least 10 µm, at least 100 µm, or at least 1.0 mm) from one another. In some embodiments, the coiled wire 200 can carry between 8 to 24 electrodes. For example, the coiled wire 200 can carry 16 electrodes. In other embodiments, the coiled wire 200 can carry between 24 and 64 electrodes 110.

In some embodiments, the wire 200 can be configured to automatically wind itself into a coiled configuration (e.g., helical pattern) when the wire 200 is deployed out of a delivery catheter. For example, the coiled wire 200 can automatically attain its coiled configuration via shape memory when the delivery catheter or sheath is retracted. The coiled configuration or shape can be a preset or shape memory shape of the wire 200 prior to the wire 200 being introduced into a delivery catheter. The preset or pre-trained shape can be made to be larger than the diameter of the anticipated deployment or implantation vessel to enable the radial force exerted by the coils to secure or position the coiled wire 200 in place within the deployment or implantation vessel.

The wire 200 can be made in part of a shape-memory alloy, a shape-memory polymer, or a combination thereof. For example, wire 200 can be made in part of Nitinol (e.g., Nitinol wire). The wire 200 can also be made in part of stainless steel, gold, platinum, nickel, titanium, tungsten, aluminum, nickel-chromium alloy, gold-palladium-rhodium alloy, chromium-nickel-molybdenum alloy, iridium, rhodium, or a combination thereof.

Figure 2B:
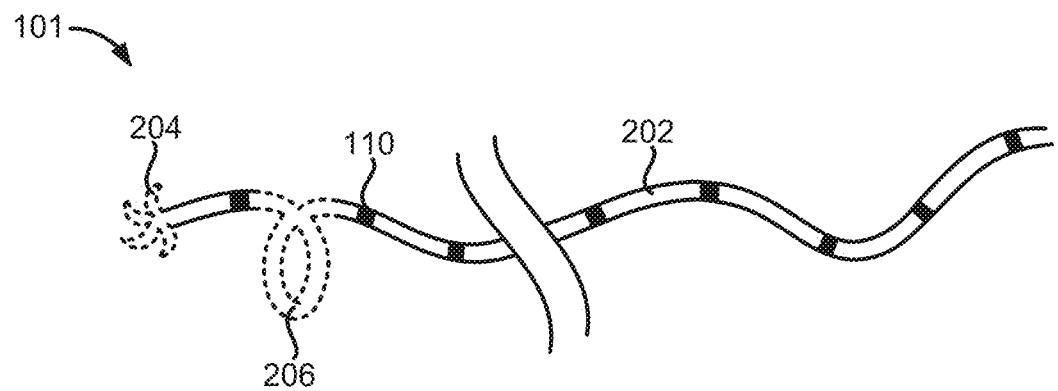
FIG. 2B illustrates yet another embodiment of an implantable recording device implemented as an anchored wire comprising a plurality of electrodes.

FIG. 2B illustrates yet another embodiment of the implantable recording device 102 as an anchored wire 202 comprising a plurality of electrodes 110. The anchored wire 202 can serve as the endovascular carrier for the electrodes 110 and can be used in vessels that are too small to accommodate either the coiled wire 200 or the stent-electrode array 108.

The anchored wire 202 can comprise a biocompatible wire or microwire attached or otherwise coupled to an anchor or another type of endovascular securement mechanism. FIG. 2B illustrates that the anchored wire 202 can comprise a barbed anchor 204, a radially-expandable anchor 206, or a combination thereof (both the barbed anchor 204 and the radially-expandable anchor 206 are shown in broken or phantom lines in FIG. 2B). In some embodiments, the barbed anchor 204 can be positioned at a distal end of the anchored wire 202. In other embodiments, the barbed anchor 204 can be positioned along one or more sides of the wire or microwire. The barbs of the barbed anchor 204 can secure or moor the anchored wire 202 to an implantation site within the subject. The radially-expandable anchor 206 can be a segment of the wire or microwire shaped as a coil or loop. The coil or loop can be sized to allow the coil or loop to conform to a vessel lumen and to expand against a lumen wall to secure the anchored wire 202 to an implantation site within the vessel. For example, the coil or loop can be sized to be larger than the diameter of the anticipated deployment or implantation vessel to enable the radial force exerted by the coil or loop to secure or position the anchored wire 202 in place within the deployment or implantation vessel.

The electrodes 110 of the anchored wire 202 can be scattered along a length of the anchored wire 202. More specifically, the electrodes 110 can be affixed, secured, or otherwise coupled to distinct points along a length of the anchored wire 202. The electrodes 110 can be separated from one another such that no two electrodes 110 are within a predetermined separation distance (e.g., at least 10 µm, at least 100 µm, or at least 1.0 mm) from one another.

In some embodiments, the anchored wire 202 can carry between 8 to 24 electrodes. For example, the anchored wire 202 can carry 16 electrodes. In other embodiments, the anchored wire 202 can carry between 24 and 64 electrodes 110.

Although FIG. 2B illustrates the anchored wire 202 having only one barbed anchor 204 and one radially-expandable anchor 206, it is contemplated by this disclosure that the anchored wire 202 can comprise a plurality of barbed anchors 204 and/or radially-expandable anchors 206.

Figure 2C:
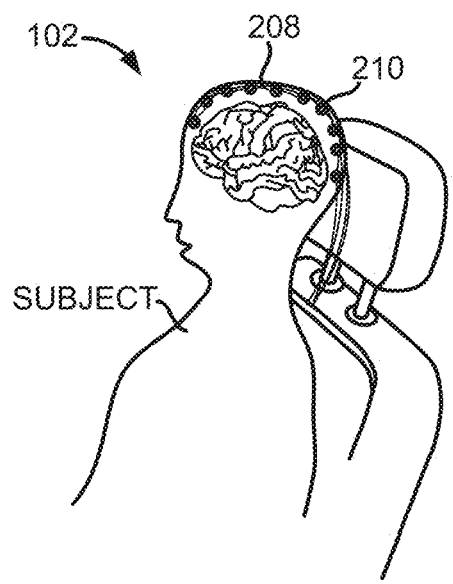
FIG. 2C illustrates one embodiment of a non-invasive recording device implemented as an electroencephalogram (EEG) device.

FIG. 2C illustrates that in another embodiment of the system 100, the recording device 102 can be a non-invasive device such as an electroencephalogram (EEG) device 208. The EEG device 208 can be a head-mounted EEG apparatus. For example, the EEG device 208 can be an EEG cap or an EEG-visor configured to be worn by the subject. The EEG device 208 can comprise a plurality of non-invasive electrodes 210 configured to be in contact with the scalp of the subject.

The EEG device 208 can comprise between 8 to 24 electrodes 210. For example, the EEG device 208 can comprise 16 electrodes 210. In other embodiments, the EEG device 208 can comprise between 24 and 64 electrodes 210.

The EEG device 208 can be used as part of the system 100 to detect one or more transient oscillatory or pseudo-oscillatory bursts 302, similar to those recorded by the implantable recording device(s) 102. For example, the EEG device 208 can capture an ongoing or real-time neural signal recording of the subject by recording raw electrical signals from the brain of the subject.

Figure 2D:
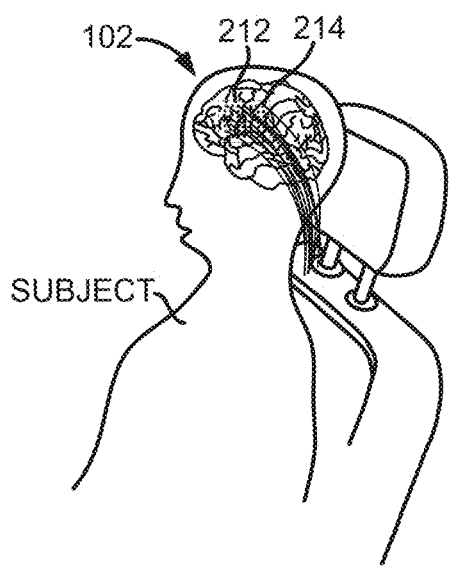
FIG. 2D illustrates an embodiment of the recording device implemented as an electrocorticography (ECoG) device.

FIG. 2D illustrates that in yet another embodiment of the system 100, the recording device 102 can be an electrocorticography (ECoG) device 212 (also referred to as an intracranial EEG device). The ECoG device 212 can be a flexible or stretchable electrode-mesh or one or more electrode patches implanted or placed on a surface of the brain of the subject. The electrode-mesh or electrode patch can comprise a plurality of electrodes 214 arranged on the mesh or patch, respectively.

The ECoG device 212 can comprise a number of electrodes 214. For example, the ECoG device 212 can comprise between 8 to 24 electrodes 214. Also, for example, the ECoG device 212 can comprise 16 electrodes 214. In other embodiments, the ECoG device 212 can comprise between 24 and 64 electrodes 214.

In some embodiments, the recording device 102 can be an implantable microelectrode array (MEA). For example, the recording device 102 can be a Utah microelectrode array or a Michigan microelectrode array.

In some embodiments, the recording device 102 can be a thin-film electrode array or comprised of thin-film microelectrodes.

Figure 3A:
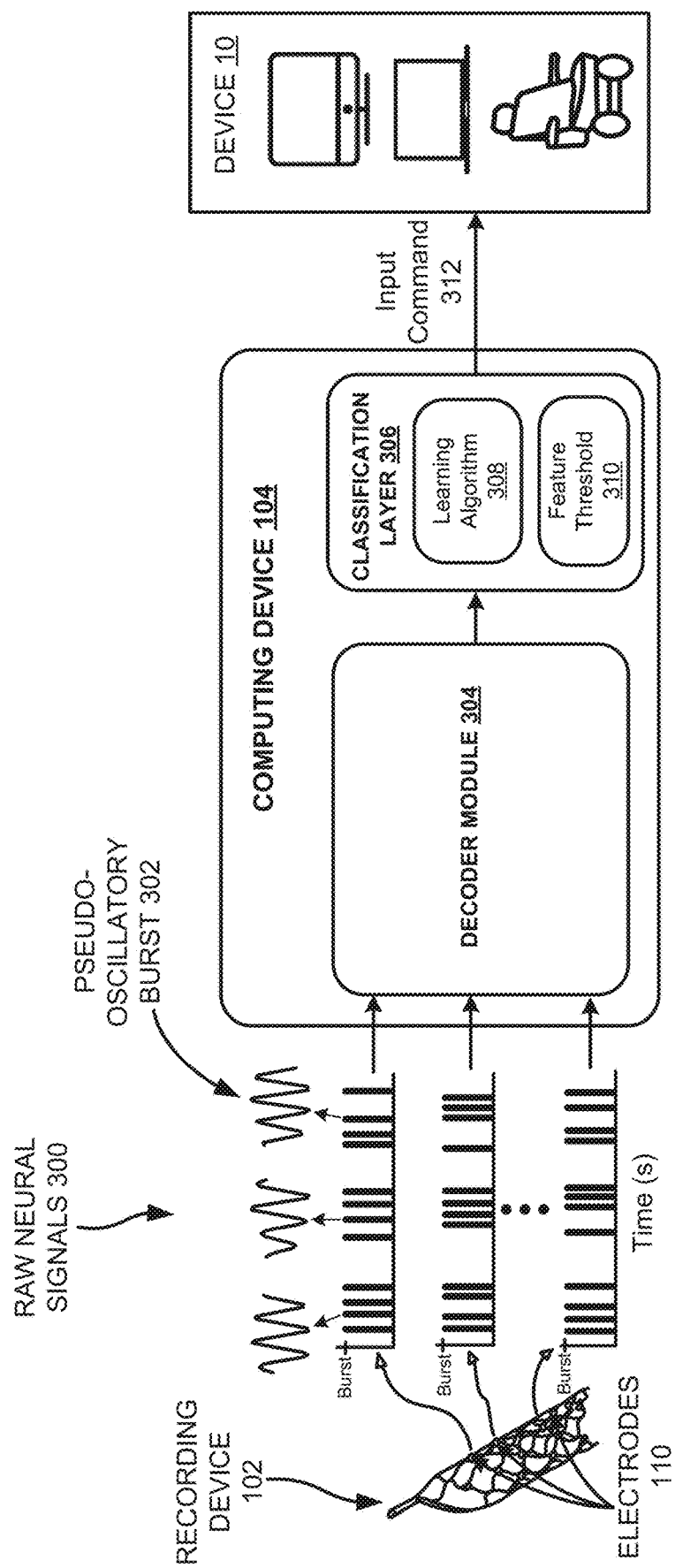
FIG. 3A illustrates the BCI system in operation.

FIG. 3A illustrates an example method of controlling a device using certain components of the system 100 disclosed herein. The method can comprise recording raw electrical signals or neural signals 300 from the brain of the subject using the recording device 102.

For example, when the recording device 102 is an implantable recording device such as the stent-electrode array 108 of FIG. 1B, the recording device 102 can comprise typically between 16 to 64 electrodes 110. Each of the electrodes 110 can record neural signals 300 at one or more frequency bands. This combination of electrodes 110 and frequency bands means that even a neural signal recording lasting only three to five seconds can comprise upwards of several thousand transient oscillatory or pseudo-oscillatory bursts 302.

The neural signals 300 captured by the electrodes 110 of the recording device 102 can be transmitted to the computing device 104 via the telemetry unit 116.

As shown in FIG. 3A, the computing device 104 can comprise a decoder module 304 and a classification layer 306 or module. The decoder module 304 can be configured to filter the raw electrical signals, converting the filtered raw electrical signals into magnitude or power-related values, and identifying a transient oscillatory or pseudo-oscillatory burst 302 each time one of the magnitude or power-related values exceeds a power threshold. The decoder module 304 can also be configured to extract one or more burst features 400 from one or more transient oscillatory or pseudo-oscillatory busts within a detection period 404 (see FIG. 4).

The classification layer 306 can be configured to predict a thought generated or conjured by the subject or a change in mental state evoked by the subject by applying at least one of a machine learning algorithm 308 (e.g., a deep learning algorithm) and a feature threshold 310 to the one or more burst features 400 extracted within the detection period 404.

As will be discussed in more detail in relation to FIG. 3B, the decoder module 304 can comprise a number of decoder sub-modules. The decoder module 304 can be configured to filter the raw electrical signals in one or more desired frequency bands (e.g., beta-band, gamma-band, alpha-band, theta-band, etc.) using one or more software filters or a wavelet convolution. For example, the decoder module 304 can comprise decoder sub-modules or instructions to filter the raw electrical signals in one or more desired frequency bands using one or more bandpass filters.

The decoder module 304 can also convert voltage values of the filtered raw electrical signals into power values for each of the desired frequency bands. Moreover, the decoder module 304 can apply a power threshold to the magnitude or power-related values for each of the desired frequency bands. The decoder module 304 can then identify one of the transient oscillatory or pseudo-oscillatory bursts 302 each time one of the magnitude or power-related values exceeds the power threshold for each of the desired frequency bands.

The decoder module 304 can also comprise sub-modules to extract one or more burst features 400 (see FIG. 4) from the one or more transient oscillatory or pseudo-oscillatory bursts 302 within the detection period 404. With the burst features 400 extracted, the classification layer 306 can then make predictions concerning the thought generated or conjured by the subject or the change in mental state of the subject by applying at least one of a machine learning algorithm 308 and a feature threshold 310 to the burst features 400 extracted within the detection period 404.

In some embodiments, the machine learning algorithm 308 can be a neural network. For example, the machine learning algorithm 308 can be a recursive neural network. As a more specific example, the classification layer 306 can use a recursive neural network such as a long short-term memory (LSTM) network to make predictions concerning the thought generated or conjured by the subject or the change in mental state evoked by the subject by feeding the burst features extracted to the LSTM network.

In other embodiments, the classification layer 306 can make predictions concerning the thought generated or conjured by the subject or the change in mental state evoked by the subject by applying a feature threshold 310 (see, also, FIG. 5A) to the burst features 400 extracted within the detection period 404.

The computing device 104 can then transmit an input command 312 associated with the prediction made by the classification layer 306 to the device 10 in order to control the device 10.

In some embodiments, the device 10 can be a separate device from the computing device 104. In these and other embodiments, the input command 312 can be a command to control one or more peripherals or hardware components of the device 10, a software application running on the device 10, or a graphic element shown on a display of the computing device 10 (e.g., a cursor, a pointer, a caret, etc.).

In other embodiments, the computing device 104 can generate an input command 312 associated with the prediction to control one or more peripherals or hardware components of the device 104, a software application running on the device 104, or a graphic element shown on a display of the computing device 104 (e.g., a cursor, a pointer, a caret, etc.).

In some embodiments, the modules of the computing device 104 (e.g., the decoder module 304, the classification layer 306, etc.) can be written using the Java™ programming language, the Python™ programming language, the C/C++ programming language, the JavaScript programming language, the Ruby™ programming language, the Matlab programing language, theC #programming language, or a combination thereof.

Figure 3B:
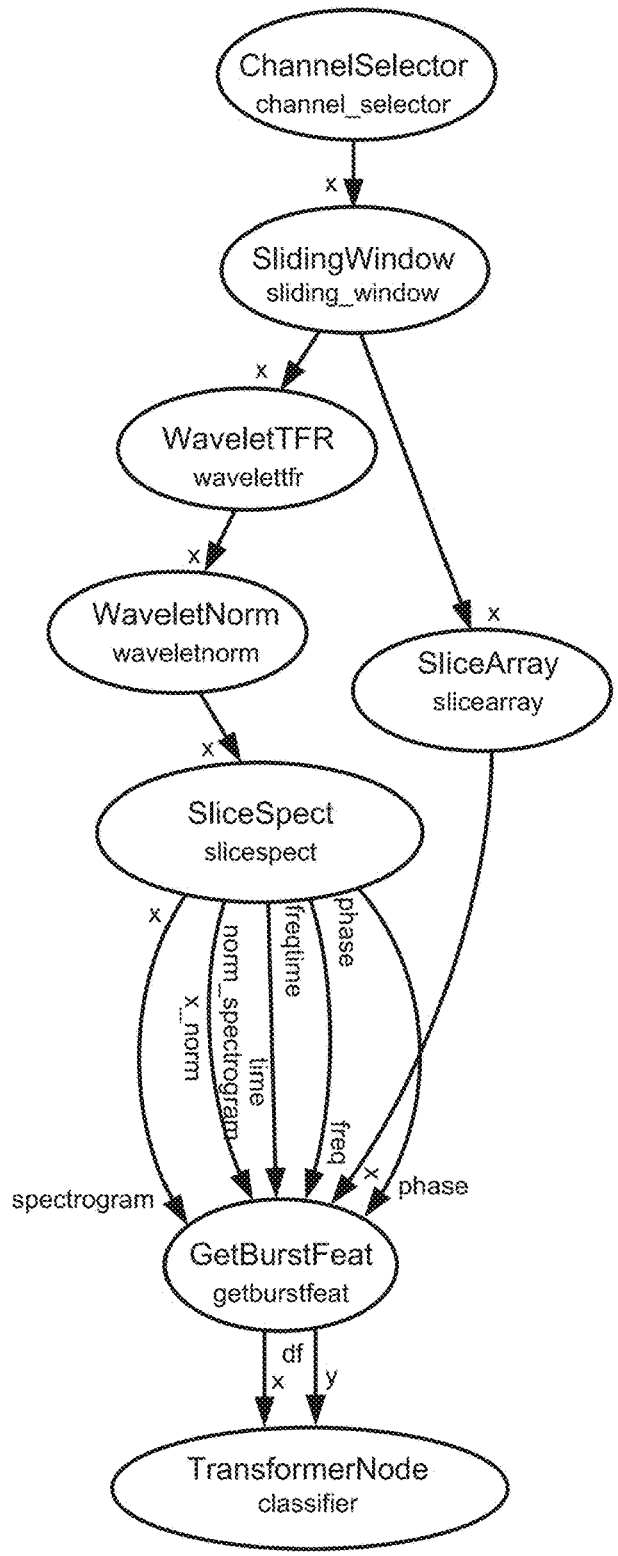
FIGS. 3B-3D illustrate example sub-modules of a decoder module.
Figure 3C:
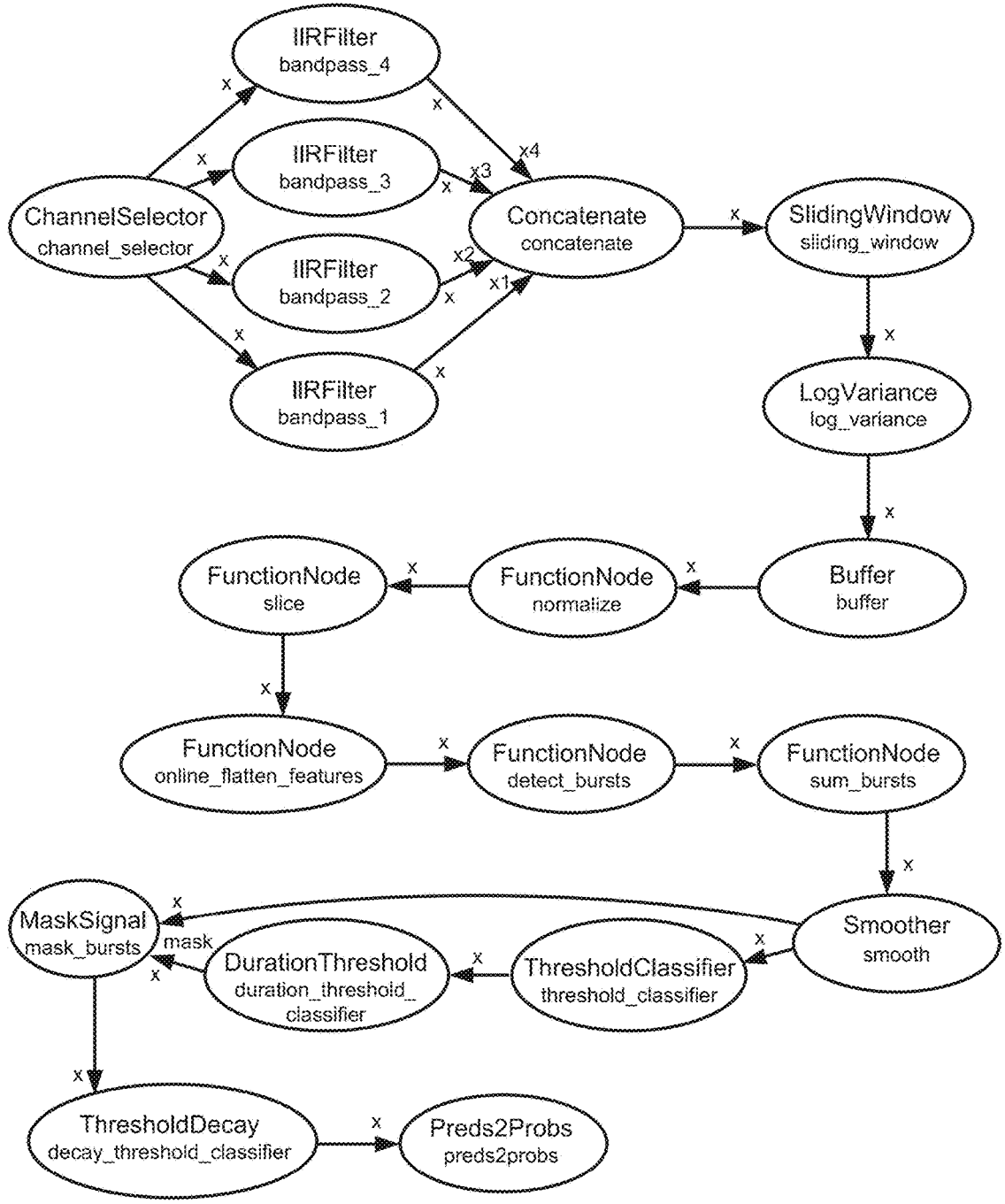
Figure 3D:
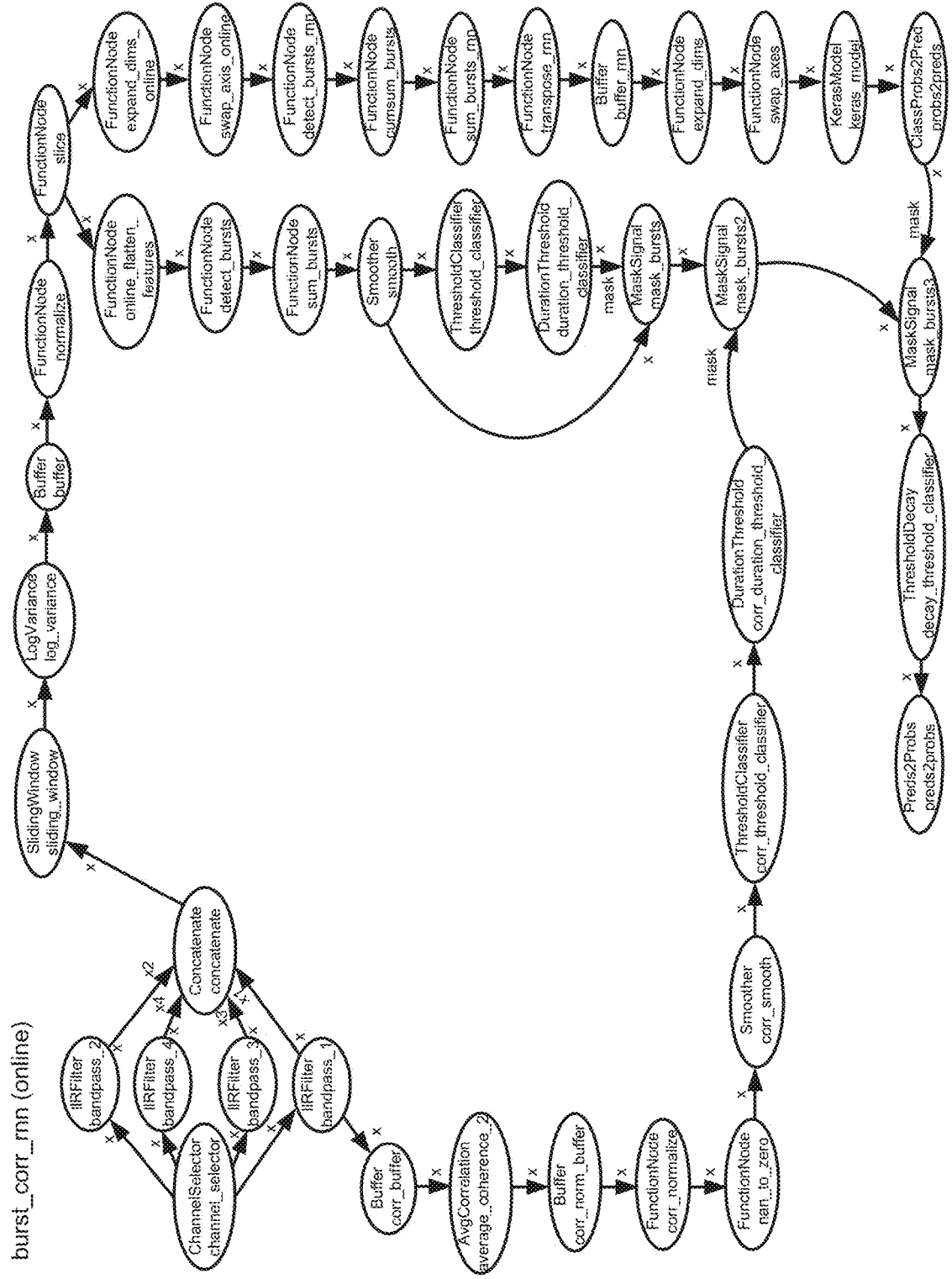

FIGS. 3B-3D illustrate example sub-modules of the decoder module 304. Each sub-module (FIGS. 3B-3D) can represent a different possible pipeline of the decoder module 304.

FIG. 3B illustrates one embodiment of a sub-module that can extract oscillatory burst features from a single event or a plurality of events using wavelet transform and pass these features to a machine learning algorithm for classification. FIG. 3C illustrates another embodiment of a sub-module that can extract oscillatory burst counts by applying several finite impulse response (FIR) filters to the signal and detect power values that exceed a pre-defined threshold for oscillatory burst detection. Another threshold may be applied to the detected bursts for classification. The latter threshold can be dynamic and require that the signal cross the threshold for a certain duration. FIG. 3D illustrates yet another embodiment of a sub-module that uses both threshold classification and machine learning algorithms.

Figure 4:
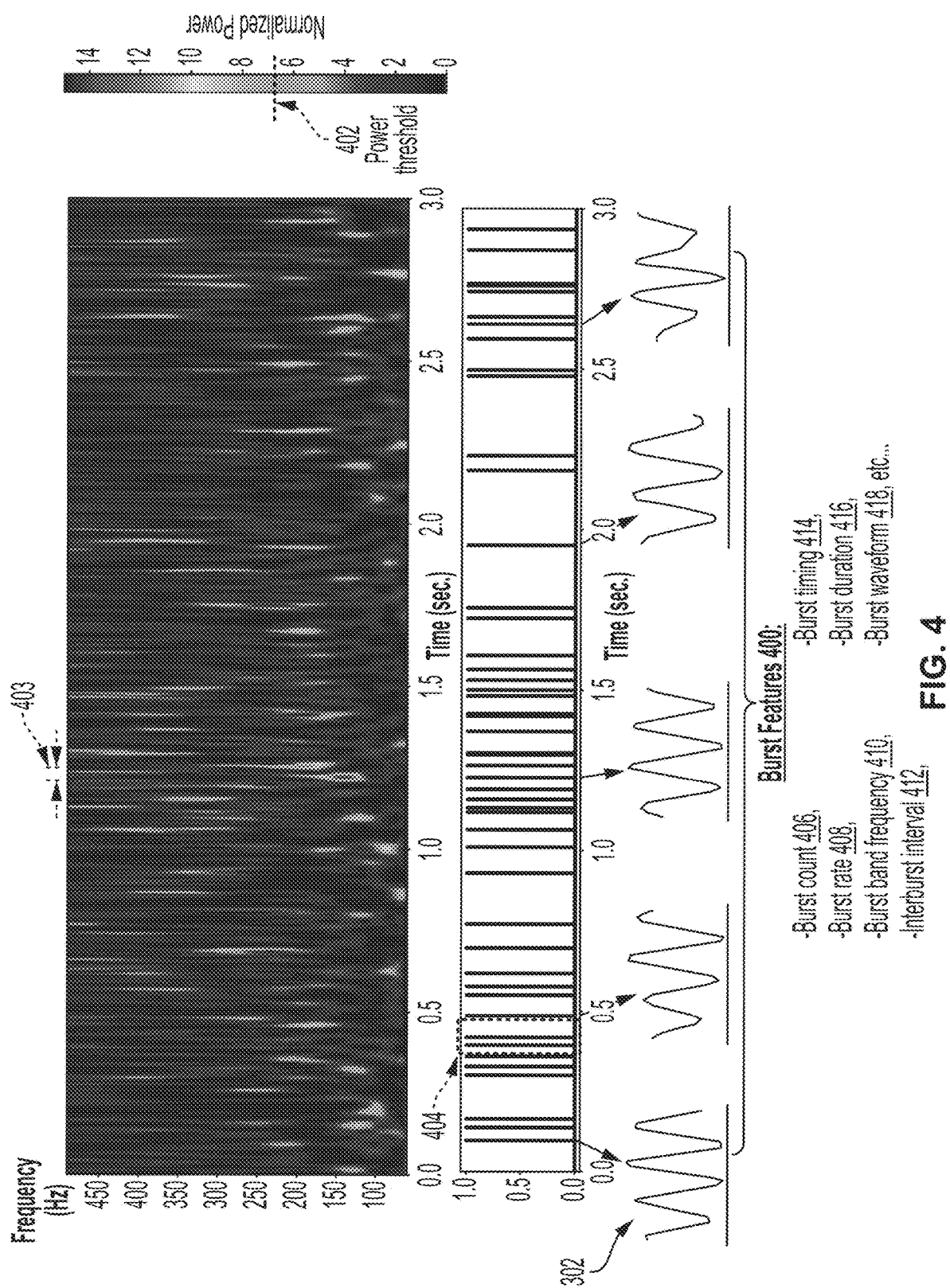
FIG. 4 illustrates example burst features that can be extracted from a neural signal recording of the subject.

FIG. 4 illustrates example burst features 400 that can be extracted from a three-second neural signal recording of the subject that has been converted into a spectrogram with power values detected at various frequency bands depicted using a color gradient. Depicted below the spectrogram is a burst timing chart showing the timing of several transient oscillatory or pseudo-oscillatory bursts 302 detected at one of the electrodes 110 of the recording device 102 or at one burst frequency during this period and example waveforms for five such bursts 302.

As previously discussed, the recording device 102 can be used to capture raw electrical signals or raw neural signals 300 from the brain of the subject. The decoder module 304 of the computing device 104 can then filter the raw electrical signals in one or more desired frequency bands using one or more bandpass filters, wavelet convolutions, or a combination thereof. The decoder module 304 can then convert voltage values of the filtered raw electrical signals into power values (expressed as $V^2/Hz$ or $\mu V^2/Hz$, dB/Hz, $S^2$ (where S denotes the units of the signal), etc.) or normalized power values (expressed as z-scores, ratios, differences, percentage changes). As a more specific example, the normalized power units in FIG. 4 can be normalized based on the median of the signal.

The decoder module 304 can then apply a power threshold 402 to the magnitude or power-related values for each of the desired frequency bands. The decoder module 304 can identify or detect one of the transient oscillatory or pseudo-oscillatory bursts 302 in response to one of the magnitude or power-related values exceeding the power threshold 402 for each of the desired frequency bands. The power threshold 402 can be selected or optimized for each user or patient.

In some embodiments, the decoder module 304 can apply a duration threshold 403 for each of the desired frequency bands. The decoder module 304 can identify or detect one of the transient oscillatory or pseudo-oscillatory bursts 302 in response to a duration of one of the raw electrical signals exceeding the duration threshold 403 for each of the desired frequency bands. The duration threshold 403 can be selected or optimized for each user or patient.

The transient oscillatory or pseudo-oscillatory bursts 302 can also be referred to in the field as "transients," "oscillation events," "[band]-bursts (e.g., beta-bursts)," "[band]-events (e.g., gamma-events)," "miniature evoked responses," or "oscillatory bursts." The oscillatory or pseudo-oscillatory bursts 302 can be characterized by being transient, meaning that each burst lasts for only a very short duration and that each burst is a high-energy burst, meaning that the power of each burst exceeds a threshold power level (the power threshold 402) determined relative to a baseline level of neural activity and/or background noise.

In some embodiments, the duration of a typical transient oscillatory or pseudo-oscillatory burst 302 can last between 1 ms to 100 ms. In other embodiments, the duration of a typical transient oscillatory or pseudo-oscillatory burst 302 can last between 10 ms and 100 ms. The duration of a transient oscillatory or pseudo-oscillatory burst 302 can depend on factors such as a frequency-band measured. For example, the transient oscillatory or pseudo-oscillatory burst 302 can last between 1 ms to 10 ms when the frequency-band measured is relatively high (e.g., gamma-band) or last greater than 10 ms when the frequency-band measured is lower (e.g., alpha-band).

Since a typical transient oscillatory or pseudo-oscillatory burst 302 is so fleeting or limited in duration, even a neural signal recording lasting only a few seconds (e.g., 3 seconds to 5 seconds) can yield thousands of oscillatory or pseudo-oscillatory bursts 302 across the various electrodes 110 of the recording device 102 and across the various desired frequency bands.

In some embodiments, the desired frequency bands can be between 0.1 Hz and 32 kHz. The desired frequency bands can also be between 4 Hz and 400 Hz. In certain embodiments, the desired frequency bands can be between 20 Hz and 200 Hz. In other embodiments, the desired frequency bands can be between 35 Hz and 150 Hz.

Each of the electrodes 110 can record neural signals 300 at one or more frequency bands. This combination of electrodes 110 and frequency bands means that even a neural signal recording lasting only three to five seconds can comprise upwards of several thousand transient oscillatory or pseudo-oscillatory bursts 302. For example, each of the electrodes 110 can record at multiple frequency bands (e.g., the entire bandwidth of neural signals) and the recordings can be decomposed into specific frequency components.

The transient oscillatory or pseudo-oscillatory bursts 302 can be distinguished from a sustained increase in power at specific frequency bands.

These transient oscillatory or pseudo-oscillatory bursts 302 can also be distinguished from action potential spike events. Action potential spikes are ubiquitous when sampled. That is, they have a characteristic response function, regardless of the thought generated or conjured by the subject or the change in mental state evoked by the subject. Transient oscillatory or pseudo-oscillatory bursts 302, on the other hand, exhibit specific burst characteristics or features that differ across mental states or differ depending on the thoughts generated or conjured by the subject. For example, the burst features detected during right-hand versus left-hand movement or movement attempts include different burst rates and other burst features, even when recorded from the same location of the brain of the subject.

The transient oscillatory or pseudo-oscillatory bursts 302 can be detected without having to (or in the absence of having to) average the results across multiple trials. That is, the transient oscillatory or pseudo-oscillatory bursts 302 can be detected from an ongoing or real-time neural signal recording of the subject. The transient oscillatory or pseudo-oscillatory bursts 302 can exhibit shorter increases in power compared to averaged data.

In some embodiments, the transient oscillatory or pseudo-oscillatory bursts 302 can be detected using a power threshold 402, a duration threshold 403, or a combination thereof. In other embodiments, the transient pseudo-oscillatory bursts 302 can be detected using Hidden Markov Models (HMMs) or template matching.

In certain embodiments, at least one of the power threshold 402 and the duration threshold 403 used to detect the transient oscillatory or pseudo-oscillatory bursts 302 can be selected or optimized based on at least one training session conducted with the subject. For example, the training session can comprise instructing or prompting the subject to generate or conjure a thought (e.g., a task-relevant thought or a task-irrelevant thought) or evoke a change in the mental state of the subject. The decoder module 304 of the computing device 104 can then record the raw neural signals 300 from the brain of the subject using the recording device 102 after prompting the subject. The decoder module 304 can then filter the raw electrical signals in the desired frequency bands using one or more frequency decomposition methods such as one or more bandpass filters, wavelet convolutions, or a combination thereof. The decoder module 304 can then convert the voltage values of the filtered raw electrical signals into power values for each of the desired frequency bands.

The computing device 104 can then determine or otherwise set the optimal power threshold 402 to be applied to the power values for each of the desired frequency bands in order to distinguish the transient oscillatory or pseudo-oscillatory bursts 302 from a baseline level of neural activity and/or background noise.

Alternatively or additionally, the computing device 104 determine or otherwise set the optimal duration threshold 403 to be applied to the raw electrical signals for each of the desired frequency bands in order to distinguish the transient oscillatory or pseudo-oscillatory bursts 302 from a baseline level of neural activity and/or background noise.

In some embodiments, at least one of the power threshold 402 and the duration threshold 403 can be determined based on a statistical quantity or statistical dispersion such as the number of standard deviations above a median or mean level of neural activity. As a more specific example, at least one of the power threshold 402 and the duration threshold 403 can be 1 to 6 standard deviations (SDs) above a mean level of neural activity.

The decoder module 304 can also extract one or more burst features 400 from the transient oscillatory or pseudo-oscillatory bursts 302 detected within a predetermined or preset detection period 404. The decoder module 304 can detect upwards of hundreds of transient oscillatory or pseudo-oscillatory bursts 302 within each detection period 404 across the various electrodes 110 of the recording device 102 and across the various frequency bands (e.g., 0.1 Hz to 32 kHz).

In some embodiments, the detection period 404 can be between 10 milliseconds (ms) and 100 ms. More specifically, the detection period 404 can be between 50 ms and 100 ms. For example, the detection period 404 can be about 100 ms.

The decoder module 304 can extract the one or more burst features 400 by counting or summing the number of transient oscillatory or pseudo-oscillatory bursts 302 detected and determining the timing of such bursts 302. The decoder module 304 can also determine the frequency, power value, and duration of each burst 302.

The burst features 400 can comprise a burst count 406, a burst rate 408, a burst band frequency 410 or frequency distribution, an interburst interval length 412 (single channel and across multiple channels), a burst timing 414 or timing pattern, an average burst duration 416, a burst waveform 418 (e.g., the time domain waveform of a burst), or any changes or combination thereof. The burst features 400 can also comprise an average power across bursts 302 within a window of time, a maximum power of the bursts 302, a number of cycles, a peak frequency of the bursts 302, a minimum frequency of the bursts 302, a maximum frequency of the bursts, a frequency span (expressed in octaves), an average power just before and/or just after a burst 302, a low-frequency instantaneous phase at the time of a high-frequency burst, alpha and beta power at the time of a high-frequency burst, an oscillatory score (i.e., a correlation between the filtered and raw signal at the time of a burst 302). The burst features can also comprise a burst synchronization or distance (i.e., a measure of the correlation between bursts at different channels when treated as a point process), the left and/or right slope of the transient bursts (i.e., how fast does the amplitude rise or fall), and repeating sequences in time of transient bursts (e.g., certain user thoughts or movement types can generate a sequence of bursts that appear at certain electrodes at specific time intervals).

Any or all such burst features 400 can be extracted from the transient oscillatory or pseudo-oscillatory bursts 302 detected within each of the detection periods 404 (e.g., between 1 ms to 100 ms).

In some embodiments, the burst rate 408 can be calculated by dividing a burst count 406 by a length of the detection period 404. The burst count 406 can be calculated by summing all of the transient oscillatory or pseudo-oscillatory bursts 302 detected across all electrodes 110, or a subset of electrodes 110, of the recording device 102 within the detection period 404. For example, the burst rate 408 for an individual channel and frequency band can range between 1 and 200 bursts per second, depending on the frequency band selected (lower frequency bands would usually exhibit a lower burst rate compared to higher frequency bands).

One unexpected discovery made by the applicants is that the burst rate 408 is a dependable and effective marker for predicting thoughts generated or conjured by the subject or changes in mental state evoked by the subject when transient oscillatory or pseudo-oscillatory bursts 302 are measured.

In certain alternative embodiments, the burst count 406 can be calculated by summing the transient oscillatory or pseudo-oscillatory bursts 302 detected across some, but not all, of the electrodes 110 of the recording device 102 within the detection period 404. For example, when the recording device 102 is an implantable recording device 102 such as the stent-electrode array 108, the burst count 406 can be calculated by summing the transient oscillatory or pseudo-oscillatory bursts 302 detected across some, but not all, of the electrodes 110 of the stent-electrode array 108.

In other embodiments, the computing device 104 can apply a weighting factor to one or more electrodes 110 of the recording device 102 (also referred to as "channels" of the recording device 102) such that the transient oscillatory or pseudo-oscillatory bursts 302 detected at such electrode(s) 110 (or channels) are weighted more (e.g., 1.5X, 2X, 3X, etc.) than the transient oscillatory or pseudo-oscillatory bursts 302 detected at another electrode 110 (or another channel) of the recording device 102. For example, the recording device 102 can be a stent-electrode array 108 comprising a plurality of electrodes 110 coupled to an expandable stent 112 or scaffold. In these embodiments, the computing device 102 can apply a weight factor to one or more electrodes 110 or channels of the stent-electrode array 108 such that the transient oscillatory or pseudo-oscillatory bursts 302 detected at such electrode(s) 110 or channels are weighted more (e.g., 1.5X, 2X, 3X, etc.) than the transient oscillatory or pseudo-oscillatory bursts 302 detected at another electrode 110 or another channel of the stent-electrode array 108.

In some embodiments, the burst feature 400 extracted can be a change in one or more of the other burst features 400 such as a change in the burst count 406, burst rate 408, burst band frequency 410, interburst interval length 412, burst timing 414, burst duration 416, or burst waveform 418 over multiple detection periods 404. In these embodiments, the change in the one or more burst features 400 can be provided as an input to the classification layer 306 to allow the classification layer 306 to make a prediction concerning the thought generated or conjured by the subject or the change in mental state evoked by the subject.

As previously discussed, the classification layer 306 of the computing device 104 can predict the thought generated or conjured by the subject or the change in mental state evoked by the subject by applying a machine learning algorithm 308 (e.g., a deep learning algorithm) to the one or more burst features 400 extracted. For example, the classification layer 306 of the computing device 104 can predict the thought generated or conjured by the subject or the change in mental state evoked by the subject by applying a machine learning algorithm 308 to the one or more burst features 400 extracted within each detection period 404.

Alternatively or additionally, the classification layer 306 of the computing device 104 can predict the thought generated or conjured by the subject or the change in mental state evoked by the subject by applying a feature threshold 310 to the one or more burst features 400 extracted. For example, the classification layer 306 of the computing device 104 can predict the thought generated or conjured by the subject or the change in mental state evoked by the subject by applying a feature threshold 310 to the one or more burst features 400 extracted within each detection period 404.

In some embodiments, the classification layer 306 can make a prediction at the end of each detection period 404. For example, a three-second recording can comprise 30 detection periods 404 and 30 predictions concerning the thoughts generated or conjured by the subject or the changes in mental state evoked by the subject.

In other embodiments, the classification layer 306 can make a prediction only when multiple detection periods 404 have passed. In these embodiments, the classification layer 306 can rely on data from the previous detection periods 404 to make the prediction.

When the burst feature 400 extracted is or includes a burst rate 408, the feature threshold 310 can be or include a burst rate threshold. For example, the classification layer 306 of the computing device 104 can make a prediction that the subject is thinking of moving a body part of the subject when the burst rate 408 calculated from the transient oscillatory or pseudo-oscillatory bursts 302 detected within a detection period 404 exceeds the burst rate threshold for that particular detection period 404.

In other embodiments, the feature threshold can be a burst count threshold when the burst feature 400 extracted is a burst count 406. Moreover, the feature threshold can be an interval length threshold when the burst feature 400 extracted is an interburst interval length 412 (an average length of time between successive bursts 302). Furthermore, the feature threshold can be a burst duration threshold when the burst feature 400 extracted is an average burst duration 416.

In some embodiments, the feature threshold can be a static threshold. For example, the feature threshold can be set or determined in advance of the subject using the system 100 after a brief training period or training session(s).

In other embodiments, the feature threshold can be a dynamic threshold. In these embodiments, the feature threshold can be adjusted over time by the computing device 102. For example, the feature threshold can be adjusted over time by the classification layer 306 of the computing device 104. The certain embodiments, the feature threshold can require crossing a threshold for a specific duration.

In certain embodiments, the feature threshold can be a median threshold amount or an average threshold amount calculated from previous detection periods 404. For example, the burst rate threshold can be a median burst rate calculated from burst rates 408 determined from previous detection periods 404. Also, for example, the burst count threshold can be a median burst count calculated from burst counts 406 determined from previous detection periods 404.

As previously discussed, the classification layer 306 can also make a prediction by passing one or more burst features 400 to a machine learning algorithm 308 running on the computing device 104. In some embodiments, the machine learning algorithm 308 can be a deep learning network such as a neural network. For example, the machine learning algorithm 308 can be a recursive neural network. As a more specific example, the classification layer 306 can use a recursive neural network such as a long short-term memory (LSTM) network to make predictions concerning the thought generated or conjured by the subject or the change in mental state evoked by the subject by feeding the burst features extracted to the LSTM network.

In some embodiments, the input(s) to the recursive neural network (RNN) (e.g., the LSTM or another RNN) can be the features extracted from the transient oscillatory or pseudo-oscillatory bursts 302 (e.g., the burst counts 406 for each electrode 110 and frequency band, the amplitude of the bursts, the specific frequencies at which the bursts occur, the waveform, or any combination thereof). The RNN can be trained using a single session or multiple sessions (where each session may include a few hundred examples) and the best model can be selected based on the accuracy of the results obtained during the training session(s). The final output of the RNN can be a prediction of a class type (e.g., a movement type or a rest state, etc.) or a probability for each class (e.g., if we select 3 classes, the output can be a 60% chance that this is a specific movement type, 20% chance that this is a different movement type, and a 20% chance that this is no-movement or the subject is in a resting state). These probabilities can be further processed by the model in order to make a final prediction.

The machine learning algorithm 308 can be trained using past predictions made by the machine learning algorithm 308 along with one or more burst features 400 extracted from previous detection periods 404. For example, the machine learning algorithm 308 can be trained using past predictions made by the machine learning algorithm 308 using burst counts 406 and/or burst rates 408. The machine learning algorithm can be trained to enhance future predictions made by the machine learning algorithm 308.

The computing device 104 can map or associate certain predictions made by the classification layer 306 to certain input command(s) 312. For example, the computing device 104 can associate a prediction made by the classification layer 306 concerning a thought generated or conjured by the subject or a change in mental state evoked by the subject to a particular input command 312. As a more specific example, the computing device 104 can associate a prediction made by the classification layer 306 concerning a thought generated or conjured by the subject to move a body part of the subject (e.g., move an ankle of the subject) to an input command 312 to initiate a click of a cursor of a personal computing device serving as the device 10.

In some embodiments, the computing device 104 can associate a first prediction concerning a first thought generated or conjured by the subject (e.g., a thought to move an ankle of the subject) to a first input command (e.g., a cursor click) and also associate a second prediction concerning a second thought generated or conjured by the subject (e.g., a thought to move an arm of the subject) to a second input command (e.g., a command to close a software application).

As previously discussed, the thought generated or conjured by the subject can be a thought related to the input command 312 or the device 10 intending to be controlled by the subject. For example, the thought generated or conjured by the subject can be a thought to move a cursor shown on a display of a personal computing device serving as the device 10 or a thought to move a mobility vehicle (e.g., a wheelchair carrying the subject) serving as the device 10. In these instances, the thought can be considered and referred to as a task-relevant thought. Moreover, the change in mental state evoked by the subject can involve the subject focusing their attention on the cursor or focusing their attention on the mobility vehicle. In these instances, the change in mental state can be referred to as a task-relevant mental state change.

In other embodiments, the thought generated or conjured by the subject can be a thought that is unrelated to or is disconnected from the input command 312 or commanding the device 10 (including any components thereof or software applications running thereon). As a more specific example, the thought generated or conjured by the subject can be a thought to move one or more body parts (e.g., hand(s), fingers, ankle(s), foot/feet, toe(s), leg(s), arm(s), head, etc.) of the subject. Also, for example, the thought generated or conjured by the subject can be a thought to tense or untense one or more body parts of the subject (e.g., tense or untense one or more muscles or muscle groups of the subject). In these instances, the thought can be referred to as a task-irrelevant thought. Moreover, the change in mental state evoked by the subject can involve the subject focusing their attention on one or more body parts of the subject or focusing their attention on a task other than commanding the device 10 (including any components thereof or software applications running thereon). In these instances, the change in mental state can be referred to as a task-irrelevant mental state change.

In some embodiments, control of the device 10 using the system 100 can be conducted asynchronously such that the subject can control the device 10 by generator or conjuring the appropriate thought or evoking the appropriate mental state change without the subject being prompted to do so in advance. In fact, one of the technical problems faced by the applicant was how to allow a subject to effectively control a device without the subject being prompted to do so. One technical solution discovered by the applicant is the system 100 and methods disclosed herein where transient oscillatory or pseudo-oscillatory bursts 302 generated in response to thoughts generated or conjured by the subject or changes in mental state evoked by the subject are detected from an ongoing or real-time neural signal recording 300 captured by a recording device 102. Burst features 400 from the transient oscillatory or pseudo-oscillatory bursts 302 detected within a detection period 404 are then extracted and predictions concerning the thoughts generated or conjured by the subject or changes in mental state evoked by the subject are made based on the burst features 400 extracted. In these embodiments, the recording device 102 is configured to continuously capture raw electrical signals or raw neural signals 300 from the brain of the subject and such signals are continuously being filtered and converted into power values and thresholds are continuously being applied to identify the transient oscillatory or pseudo-oscillatory bursts 302 within each detection period 404. Predictions are then made by a classification layer 306 of the computing device 104 at the end of each detection period 404 concerning whether the subject intended to transmit an input command to the device 10.

Alternatively, control of the device 10 using the system 100 can be conducted synchronously such that the subject can control the device 10 by generating or conjuring the appropriate thought or evoking the appropriate mental state change in response to being prompted or instructed to do so by the computing device 104, the telemetry unit 116, or another device. In these embodiments, one or more detection periods 404 can begin once the subject has been prompted or instructed to generate or conjure the appropriate thought or evoke the appropriate mental state change. One unexpected discovery made by the applicant is that certain burst features 400 such as the interburst interval length 412 or the burst timing 414 or timing pattern may be used to predict the thought generated or conjured by the subject or the change in mental state evoked by the subject when control of the device 10 is conducted synchronously.

Figure 5A:
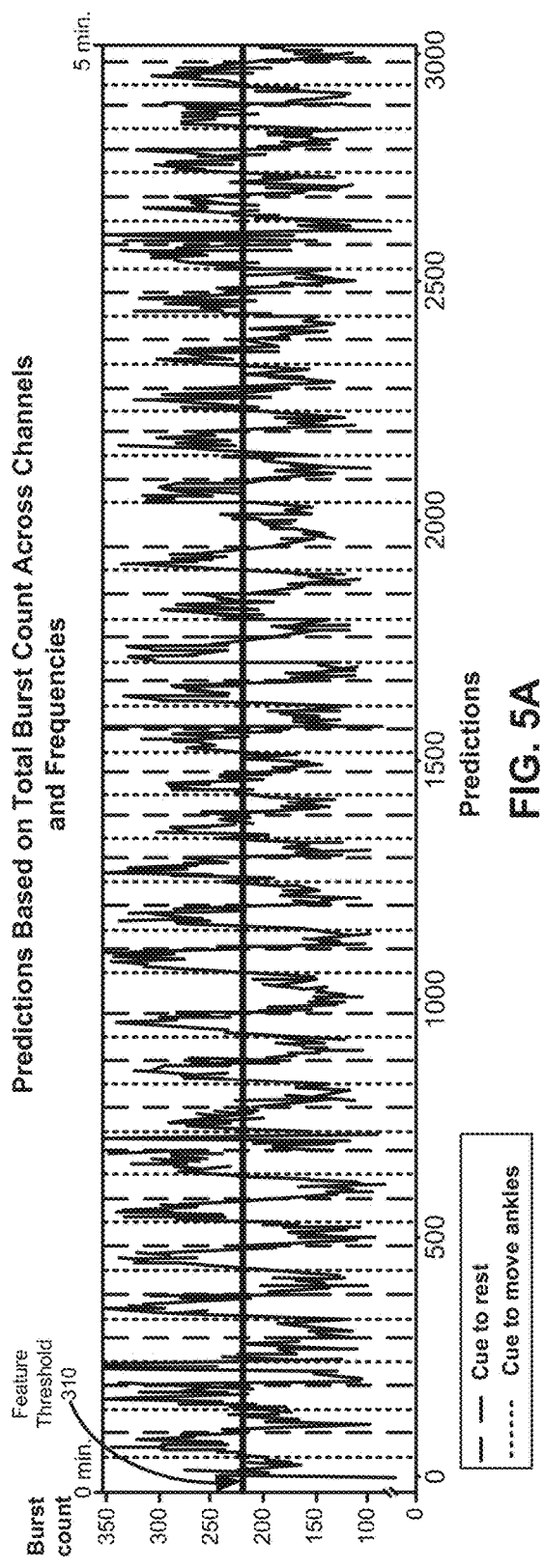
FIG. 5A is a graph illustrating a total burst count across all channels of the recording device and across all burst frequencies as a function of predictions made.
Figure 5B:
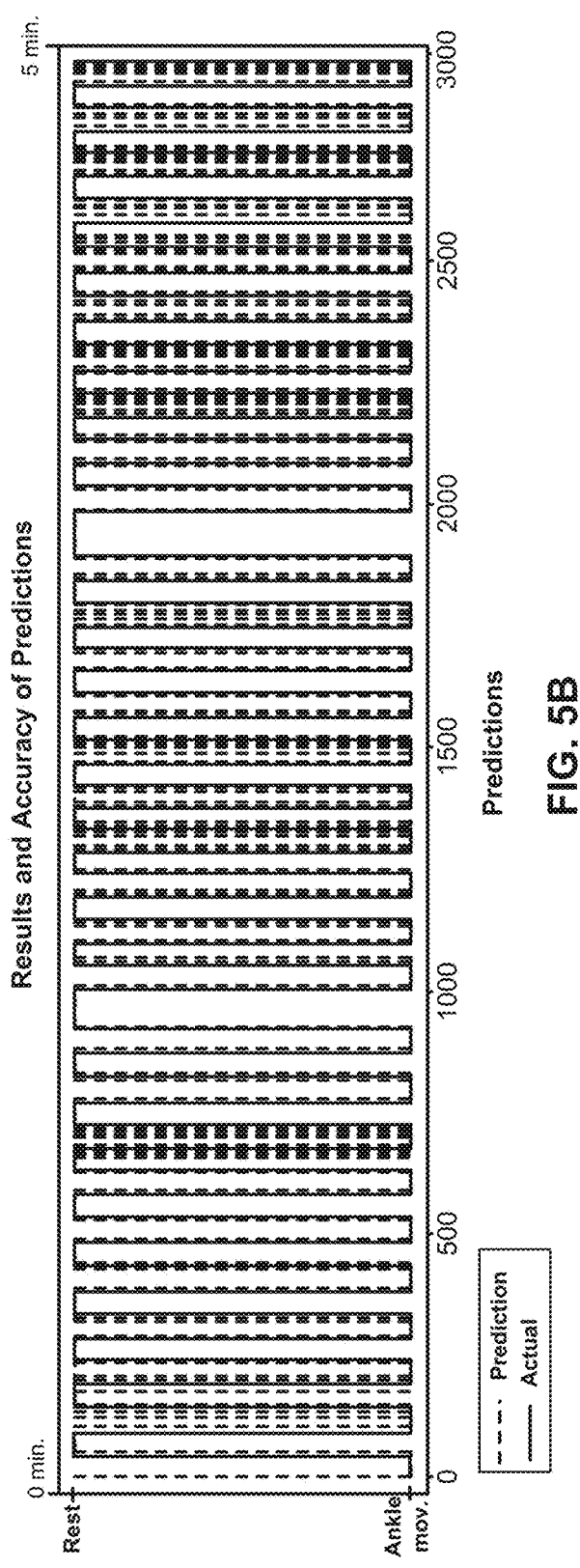
FIG. 5B is a step chart showing the results and accuracy of the predictions over time.

FIG. 5A is a graph illustrating a total burst count across all channels (or electrodes 110) of the recording device 102 and across all burst frequencies as a function of predictions made. FIG. 5B is a step chart showing the results and accuracy of the predictions.

As shown in FIG. 5A, a total of 3000 predictions can be made during this five-minute recording with a prediction being made at the end of each 100 ms detection period 404. A burst count threshold can be set as the feature threshold 310. For example, the burst count threshold can be approximately 220 bursts across all channels and burst frequencies.

In this example, the recording device 102 can be an implantable recording device such as the stent-electrode array 108. The total number of transient oscillatory or pseudo-oscillatory bursts 302 detected across all electrodes 110, or a subset of electrodes 110, of the stent-electrode array 108 and across all frequencies (e.g., 0.1 Hz to 32 kHz) can be counted at the end of each detection period 404. When the total burst count exceeds the burst count threshold, the classification layer 306 of the computing device 104 can predict that the subject attempted to move or conjured a thought to move the ankle of the subject. When the total burst count did not exceed the burst count threshold during a detection period 404, the classification layer 306 of the computing device 104 predicted that the mental state of the subject was that of a rest state.

FIGS. 5A and 5B also illustrate that the accuracy of the predictions can be determined by periodically providing a cue or prompt to the subject to either move the subject's ankle or maintain/achieve a rest state. Predictions made after the cue can be used to determine the accuracy of the predictions. For example, FIG. 5B shows that the computing device 104 was highly accurate in its prediction of the subject in a rest state but was slightly less accurate when predicting the subject attempting to move the subject's ankle or generating/conjuring a thought to move the subject's ankle. This result is acceptable given that slightly less accurate predictions of the rest state or null action would merely result in some instances of the input command 312 not being transmitted when desired by the subject during one or more detection periods 404. Since the detection periods 404 are only between about 1 ms to 100 ms, a missed or deficient input command can simply be cured by a subsequent or ensuing input command transmission (that is, if a subject intends to click a cursor and the subject's intention is missed during one detection period, the click can be detected in an ensuing detection period with result being that the subject may not even perceive the delay or consider it caused by machine latency). The opposite result (i.e., the computing device 104 not being able to accurately detect the rest state) would not be acceptable as this would cause the system 100 to transmit input commands 312 (e.g., cursor clicks or user inputs) when not desired by the subject.

FIGS. 5A and 5B illustrate that the system 100 and methods disclosed herein can be used to accurately transmit input commands 312 to control a device 10 based on the detection of transient oscillatory or pseudo-oscillatory bursts 302 from an ongoing or real-time neural signal recording.

Figure 6:
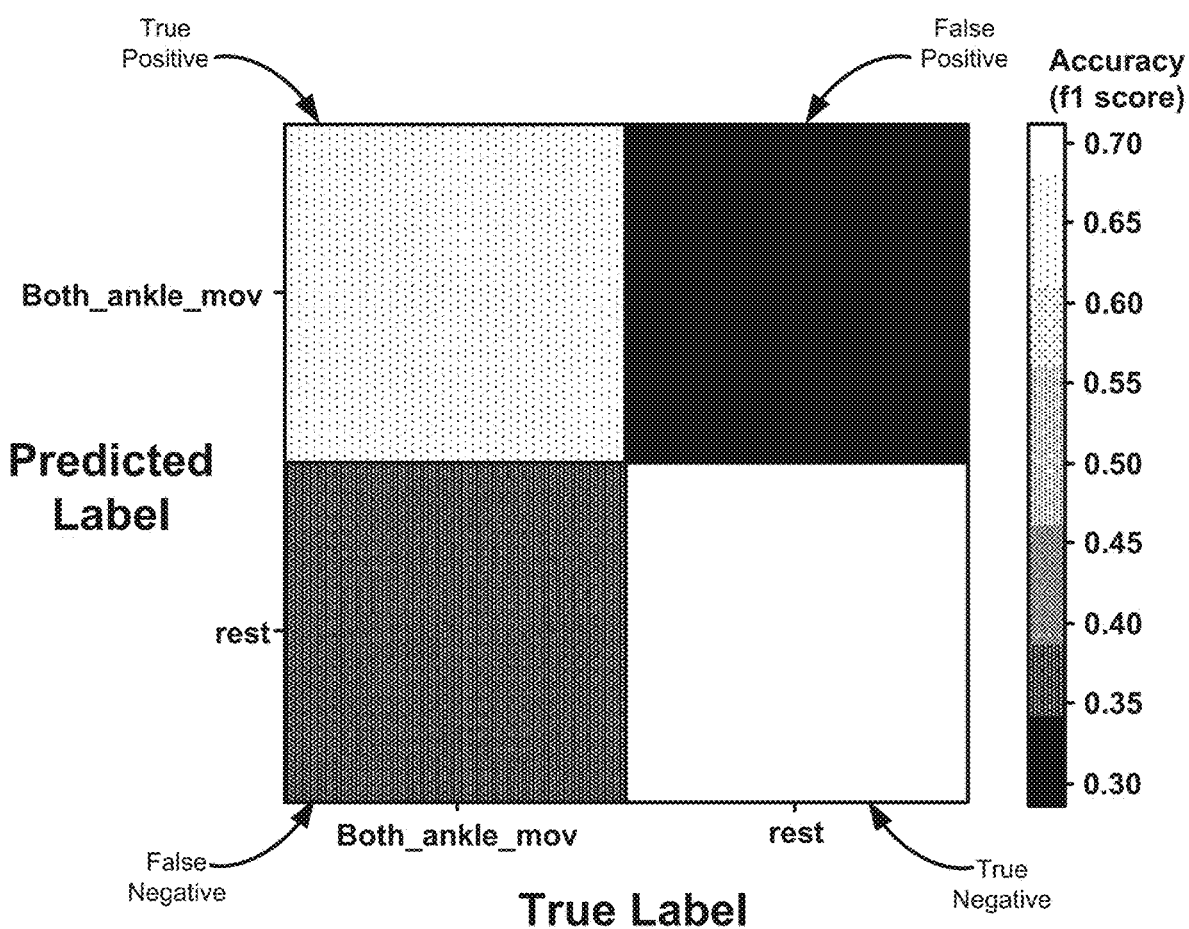
FIG. 6 illustrates a confusion matrix showing the classification accuracy of predictions made by the BCI system.

FIG. 6 illustrates a confusion matrix showing the classification accuracy of predictions made by the system 100 concerning thoughts generated or conjured by the subject or changes in mental state evoked by the subject. For example, as shown in FIG. 6, the thoughts generated or conjured by the subject or the changes in mental state evoked by the subject relate to movement of both of the subject's ankles. When the subject is not generating or conjuring such thoughts or evoking such changes in their mental state, the subject achieved or remained in a rest state.

In order to generate this confusion matrix, a total of 15 burst features 400 were extracted from the numerous transient oscillatory or pseudo-oscillatory bursts 302 detected from a 10-minute neural signal recording of the subject. For example, the 15 burst features 400 can be selected from the following list of burst features 400: a burst count 406, a burst rate 408, a burst band frequency 410 or frequency distribution, an interburst interval length 412 (single channel and across multiple channels), a burst timing 414 or timing pattern, an average burst duration 416, a burst waveform 418 (e.g., the time domain waveform of a burst), an average power across bursts 302 within a window of time, a maximum power of the bursts 302, a number of cycles, a peak frequency of the bursts 302, a minimum frequency of the bursts 302, a maximum frequency of the bursts, a frequency span (expressed in octaves), an average power just before and/or just after a burst 302, a low-frequency instantaneous phase at the time of a high-frequency burst, alpha and beta power at the time of a high-frequency burst, an oscillatory score (i.e., a correlation between the filtered and raw signal at the time of a burst 302), a burst synchronization or distance (i.e., a measure of the correlation between bursts at different channels when treated as a point process), the left and/or right slope of the transient bursts (i.e., how fast does the amplitude rise or fall), and repeating sequences in time of transient bursts (e.g., certain user thoughts or movement types can generate a sequence of bursts that appear at certain electrodes at specific time intervals).

As shown in FIG. 6, the system 100 was most accurate (with an f1 score of about 0.70) in predicting that the subject was in a rest state when the subject was actually in such a state. This prediction can be considered the true negative prediction.

The system 100 was slightly less accurate (with an f1 score of about 0.65) in predicting that the subject was generating or conjuring a thought or evoking a change in the mental state of the subject related to moving both of the subject's ankles when the subject was actually generating/conjuring such a thought or evoking such a change in the mental state of the subject. This prediction can be considered the true positive prediction.

The system 100 was not as likely to predict that the subject was in a rest state when the subject was actually generating/conjuring a thought or evoking a change in the mental state of the subject related to moving both of the subject's ankles. This prediction can be considered the false negative prediction.

The system 100 was least likely to predict that the subject was generating/conjuring a thought or evoking a change in the mental state of the subject related to moving both of the subject's ankles when the subject was actually in a rest state. This prediction can be considered the false positive prediction. The objective of any effective BCI system 100 is to minimize false positive predictions. This is because false positive predictions would interfere the most with a subject's use of the BCI system 100 as the system 100 would inadvertently transmit input commands 312 to a device 10 (resulting in inadvertent cursor clicks or user inputs) when the subject had no such desire to do so.

Figures 7A, 7B:
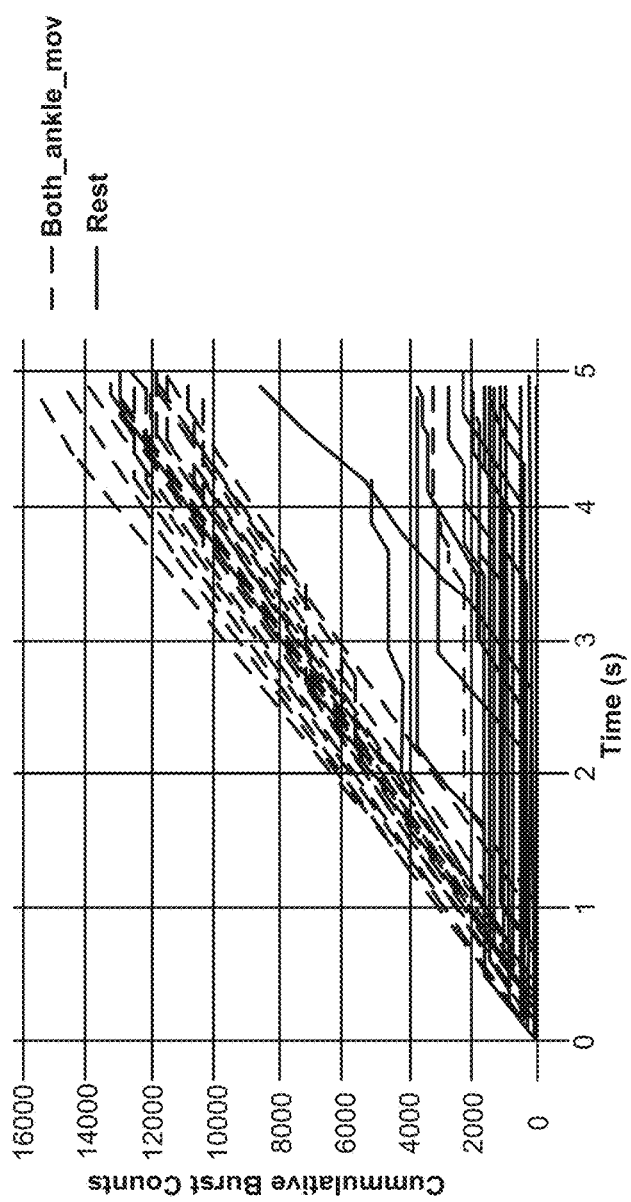
FIG. 7A is a graph illustrating cumulative burst counts across all channels of the recording device over a five-second period.
FIG. 7B is a classification report indicating the precision, recall, and f1 scores of predictions made by the BCI system using transient oscillatory or pseudo-oscillatory bursts detected from a 5-minute neural signal recording of the subject.

FIG. 7A is a graph illustrating cumulative burst counts across all channels of the recording device 102 over a five-second period. The subject was instructed to either generate/conjure a thought to move both of the subject's ankles or remain in a rest state for the five-second period. All transient oscillatory or pseudo-oscillatory bursts 302 detected across all channels or electrodes 110 of the recording device 102 were counted during this five-second period. FIG. 7A illustrates that, with rare exceptions, numerous transient oscillatory or pseudo-oscillatory bursts 302 were detected in response to the subject generating or conjuring a thought to move both of the subject's ankles while the amount of such bursts 302 decreased significantly when the subject remained in the rest state.

FIG. 7B is a classification report indicating the precision, recall, and f1 scores of predictions made by the system 100 using transient oscillatory or pseudo-oscillatory bursts 302 detected from a 5-minute neural signal recording of the subject. The f1 score is an error metric which measures the performance or accuracy of a classification model or classification layer 306. The f1 score provides insights into the ability of a classification model or classification layer 306 to capture positive cases (recall) and the accuracy of the cases it does capture (precision). The relatively high f1 scores shown in FIG. 7B indicate that the subject can reliably control a device 10 with high accuracy at a click-rate greater than 3 clicks per second.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

The term "engine" or "module" as used herein can refer to software, firmware, hardware, or a combination thereof. In the case of a software implementation, for instance, these may represent program code that performs specified tasks when executed on a processor (e.g., CPU, GPU, or processor cores therein). The program code can be stored in one or more computer-readable memory or storage devices. Any references to a function, task, or operation performed by an "engine" or "module" can also refer to one or more processors of a device or server programmed to execute such program code to perform the function, task, or operation.

It will be understood by one of ordinary skill in the art that the various methods disclosed herein may be embodied in a non-transitory readable medium, machine-readable medium, and/or a machine accessible medium comprising instructions compatible, readable, and/or executable by a processor or server processor of a machine, device, or computing device. The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A method of controlling a device, comprising:
   detecting one or more transient oscillatory or pseudo-oscillatory bursts from an ongoing neural signal recording of a subject captured by a recording device, wherein the one or more transient oscillatory or pseudo-oscillatory bursts are generated in response to a thought generated by the subject or a change in mental state evoked by the subject;

extracting, using one or more processors of a computing device communicatively coupled to the recording device, one or more burst features from the one or more transient oscillatory or pseudo-oscillatory bursts detected within a detection period of between 1 ms and 100 ms;

inputting the one or more burst features extracted within the detection period to a machine learning algorithm to obtain as an output from the machine learning algorithm a prediction concerning the thought generated by the subject or the change in mental state evoked by the subject; and controlling the device with an input command based on the prediction, wherein the device is a computing device, a mobility vehicle, a peripheral device of the computing device, or a software application running on the computing device.

2. The method of claim 1, wherein the ongoing neural signal recording of the subject is made by recording raw electrical signals from the brain of the subject using the recording device, and wherein detecting the one or more transient oscillatory or pseudo-oscillatory bursts further comprises:

filtering the raw electrical signals in one or more desired frequency bands using one or more frequency decomposition methods;

converting voltage values of the filtered raw electrical signals into magnitude or power-related values for each of the desired frequency bands;

applying at least one of a power threshold to the magnitude or power-related values for each of the desired frequency bands and a duration threshold for each of the desired frequency bands; and identifying one of the transient oscillatory or pseudo-oscillatory bursts in response to at least one of the magnitude or power-related values exceeding the power threshold and the filtered raw electrical signals exceeding the duration threshold for each of the desired frequency bands.

3. The method of claim 2, wherein the at least one of the power threshold and the duration threshold is selected based on at least one training session conducted with the subject, wherein the at least one training session comprises:

instructing or prompting the subject to generate the thought or evoke the change in the mental state of the subject;

recording the raw electrical signals from the brain of the subject using the recording device after prompting the subject to generate the thought;

filtering the raw electrical signals in the one or more desired frequency bands using one or more frequency decomposition methods;

converting the voltage values of the filtered raw electrical signals into power values for each of the desired frequency bands; and selecting the at least one of the power threshold and the duration threshold to be applied for each of the desired frequency bands in order to distinguish the transient oscillatory or pseudo-oscillatory bursts from background noise.

4. The method of claim 2, wherein the desired frequency bands comprise frequency bands between 0.1 Hz and 32 kHz.

5. The method of claim 2, wherein the desired frequency bands comprise at least one of a beta frequency band, a gamma frequency band, and a high-gamma frequency band.

6. The method of claim 1, wherein the one or more burst features comprises a burst rate, wherein the burst rate is calculated by dividing a burst count by a length of the detection period.

7. The method of claim 6, wherein the burst count is calculated by summing all of the transient oscillatory or pseudo-oscillatory bursts detected across all electrodes or a subset of electrodes of the recording device within the detection period.

8. The method of claim 1, wherein the machine learning algorithm is a neural network.

9. The method of claim 8, wherein the neural network is a recursive neural network.

10. The method of claim 9, wherein the recursive neural network is a long short-term memory (LSTM) neural network.

11. The method of claim 1, wherein the device is at least one of a personal computing device, and an internet-of-things (IoT) device.

12. The method of claim 1, wherein the thought of the subject is a thought generated by the subject to move one or more body parts of the subject.

13. The method of claim 1, wherein the thought is generated by the subject without the subject being prompted to do so such that control of the device is conducted asynchronously.

14. The method of claim 1, wherein the recording device is an invasive recording device.

15. The method of claim 14, wherein the recording device is an endovascular recording device comprising a plurality of electrodes carried by an endovascular carrier configured to be implanted within a vein or sinus of the brain of the subject.

16. The method of claim 15, wherein the one or more transient oscillatory or pseudo-oscillatory bursts are detected using the electrodes carried by the endovascular carrier, and wherein the method further comprises applying a weighting factor to one or more electrodes of the endovascular carrier such that the transient oscillatory or pseudo-oscillatory bursts detected at the one or more electrodes is weighted more than the transient oscillatory or pseudo-oscillatory bursts detected at another electrode of the endovascular carrier.

17. The method of claim 14, wherein the recording device is an implantable microelectrode array.

18. The method of claim 17, wherein the recording device is a Utah microelectrode array.

19. The method of claim 14, wherein the recording device is a thin-film electrode array.

20. The method of claim 1, further comprising training the machine learning algorithm using previous predictions made by the machine learning algorithm and the burst features extracted from previous detection periods to enhance predictions made by the machine learning algorithm.

21. The method of claim 1, wherein the one or more burst features is a burst count or change thereof.

22. The method of claim 1, wherein the one or more burst features is an interburst interval length or change thereof.

23. The method of claim 1, wherein the one or more burst features is a burst timing pattern or change thereof.

24. The method of claim 1, wherein the one or more burst features is a time domain waveform of a burst or change thereof.

25. A system for controlling a device, comprising:
a recording device configured to capture an ongoing neural signal recording of a subject; and a computing device having one or more processors communicatively coupled to the recording device, wherein the one or more processors are programmed to:
- detect one or more transient oscillatory or pseudo-oscillatory bursts from the ongoing neural signal recording of the subject, wherein the one or more transient oscillatory or pseudo-oscillatory bursts are generated in response to a thought generated by the subject or a change in mental state evoked by the subject,
- extract one or more burst features from the one or more transient oscillatory or pseudo-oscillatory bursts detected within a detection period of between 1 ms and 100 ms,
- input the one or more burst features extracted within the detection period to a machine learning algorithm to obtain as an output from the machine learning algorithm a prediction concerning the thought generated by the subject or the change in mental state evoked by the subject,
- and control the device via an input command transmitted to the device, wherein the device is a computing device, a mobility vehicle, a peripheral device of the computing device, or a software application running on the computing device, and wherein the input command is based on the prediction.

26. A method of controlling a device, comprising:
- detecting one or more transient oscillatory or pseudo-oscillatory bursts from an ongoing neural signal recording of a subject captured by a recording device, wherein the one or more transient oscillatory or pseudo-oscillatory bursts are generated in response to a thought generated by the subject or a change in mental state evoked by the subject;
- extracting, using one or more processors of a computing device communicatively coupled to the recording device, one or more burst features from the one or more transient oscillatory or pseudo-oscillatory bursts detected within a detection period of between 1 ms and 100 ms;
- applying a feature threshold to the one or more burst features extracted within the detection period using the one or more processors of the computing device;
- determining, using the one or more processors of the computing device, the thought generated by the subject or the change in mental state evoked by the subject when the one or more burst features extracted within the detection period meets or exceeds the feature threshold; and
- and controlling the device with an input command based on the prediction, wherein the device is a computing device, a mobility vehicle, a peripheral device of the computing device, or a software application running on the computing device.

27. The method of claim 26, wherein the feature threshold is a burst rate threshold.

28. The method of claim 27, wherein the burst rate threshold is a median burst rate calculated from previous detection periods.

29. The method of claim 26, wherein the feature threshold is a dynamic threshold adjusted over time by the computing device.

* * * * *